US010617666B2

(12) United States Patent
Reiche et al.

(10) Patent No.: US 10,617,666 B2
(45) Date of Patent: Apr. 14, 2020

(54) TREATMENT OF METABOLIC DISORDERS IN FELINE ANIMALS

(71) Applicant: Boehringer Ingelheim Vetmedica GmbH, Ingelheim am Rhein (DE)

(72) Inventors: Dania Birte Reiche, Bingen am Rhein (DE); Silke Haag-Diergarten, Frankfurt am Main (DE); Leah Jeanette Hennings, Kansas City, MO (US); Saskia Kley, Appenheim (DE); Anne M. Traas, Saint Joseph, MO (US)

(*) Notice: Subject to any disclaimer, the term of this patent is extended or adjusted under 35 U.S.C. 154(b) by 148 days.

(21) Appl. No.: 14/573,352

(22) Filed: Dec. 17, 2014

(65) Prior Publication Data

US 2015/0164856 A1 Jun. 18, 2015

(30) Foreign Application Priority Data

Dec. 17, 2013 (EP) .................................. 13197821
Oct. 1, 2014 (EP) .................................. 14187228

(51) Int. Cl.
*A61K 31/351* (2006.01)
*A61K 38/28* (2006.01)
*A61K 31/7034* (2006.01)
*C07D 309/10* (2006.01)
*C07H 7/04* (2006.01)

(52) U.S. Cl.
CPC ........ *A61K 31/351* (2013.01); *A61K 31/7034* (2013.01); *A61K 38/28* (2013.01); *C07D 309/10* (2013.01); *C07H 7/04* (2013.01)

(58) Field of Classification Search
None
See application file for complete search history.

(56) References Cited

U.S. PATENT DOCUMENTS

| | | | |
|---|---|---|---|
| 7,371,732 B2 | 5/2008 | Eickelmann et al. | |
| 7,375,090 B2 | 5/2008 | Himmelsbach et al. | |
| 7,393,836 B2 | 7/2008 | Eckhardt et al. | |
| 7,417,032 B2 | 8/2008 | Eckhardt et al. | |
| 7,419,959 B2 | 9/2008 | Eckhardt et al. | |
| 7,524,822 B2 | 4/2009 | Kraemer et al. | |
| 7,579,449 B2 | 8/2009 | Eckhardt et al. | |
| 7,589,193 B2 | 9/2009 | Washburn et al. | |
| 7,683,160 B2 | 3/2010 | Eckhardt et al. | |
| 7,687,469 B2 | 3/2010 | Eckhardt et al. | |
| 7,713,938 B2 | 5/2010 | Himmelsbach et al. | |
| 7,723,309 B2 | 5/2010 | Himmelsbach et al. | |
| 7,745,414 B2 | 6/2010 | Eckhardt et al. | |
| 7,772,191 B2 | 8/2010 | Eckhardt et al. | |
| 7,772,378 B2 | 8/2010 | Himmelsbach et al. | |
| 7,776,830 B2 | 8/2010 | Eckhardt et al. | |
| 7,847,074 B2 | 12/2010 | Eckhardt et al. | |
| 7,851,502 B2 * | 12/2010 | Bindra ................. | A61K 9/1652 424/451 |
| 7,851,602 B2 | 12/2010 | Himmelsbach et al. | |
| 7,858,587 B2 | 12/2010 | Eckhardt et al. | |
| 7,879,806 B2 | 2/2011 | Himmelsbach et al. | |
| 7,879,807 B2 | 2/2011 | Himmelsbach et al. | |
| 8,039,441 B2 | 10/2011 | Himmelsbach et al. | |
| 8,080,580 B2 | 12/2011 | Mascitti et al. | |
| 8,283,326 B2 | 10/2012 | Eckhardt et al. | |
| 8,283,454 B2 | 10/2012 | Liou et al. | |
| 8,507,450 B2 | 8/2013 | Eckhardt et al. | |
| 8,551,957 B2 | 10/2013 | Dugi et al. | |
| 8,987,323 B2 | 3/2015 | Cai et al. | |
| 9,145,434 B2 * | 9/2015 | Eckhardt ................ | C07H 15/26 |
| 2003/0064935 A1 | 4/2003 | Gougoutas | |
| 2007/0259821 A1 | 11/2007 | Eckhardt et al. | |
| 2009/0143316 A1 | 6/2009 | Imamura et al. | |
| 2010/0167988 A1 * | 7/2010 | Gant ..................... | C07B 59/002 514/1.1 |
| 2010/0167989 A1 | 7/2010 | Gant | |
| 2010/0249392 A1 | 9/2010 | Eckhardt et al. | |

(Continued)

FOREIGN PATENT DOCUMENTS

| | | |
|---|---|---|
| CA | 2519584 A1 | 9/2004 |
| EP | 2048150 A1 | 4/2009 |

(Continued)

OTHER PUBLICATIONS

Jamil et al., "Acid Maltase Deficiency—Pompe's Disease" J Pak Med Assoc (2011) vol. 61 No. 8, pp. 821-823.*
Bélanger-Quintana et al., "Up to date knowledge on different treatment strategies for phenylketonuria" Mol Genet Metab (2011) vol. 104 No. 0, pp. S19-S25.*
Zafeiriou et al., "Brain and Spinal MR Imaging Findings in Mucopolysaccharidoses: A Review" Am J Neuroradiol (2013) vol. 34 pp. 5-13.*
Sidransky et al., "Gaucher Disease: Insights from a Rare Mendelian Disorder" Discov Med (2012) vol. 14 No. 77 pp. 273-281.*
Carrillo-Carrasco et al., "Disorders of Intracellular Cobalamin Metabolism" Genereviews (2008) downloaded from NCBI Bookshelf, pp. 1-30.*
Mew et al., "Urea Cycle Disorders Overview" Genereviews (2003) downloaded from NCBI Bookshelf pp. 1-24.*

(Continued)

*Primary Examiner* — Eric Olson
(74) *Attorney, Agent, or Firm* — Judy Jarecki-Black

(57) ABSTRACT

The present invention relates to one or more SGLT2 inhibitors or pharmaceutically acceptable forms thereof for use in the treatment and/or prevention of a metabolic disorder in a feline animal, preferably wherein the metabolic disorder is one or more selected from the group consisting of: ketoacidosis, pre-diabetes, diabetes mellitus type 1 or type 2, insulin resistance, obesity, hyperglycemia, impaired glucose tolerance, hyperinsulinemia, dyslipidemia, dysadipokinemia, subclinical inflammation, systemic inflammation, low grade systemic inflammation, hepatic lipidosis, atherosclerosis, inflammation of the pancreas, neuropathy and/or Syndrome X (metabolic syndrome) and/or loss of pancreatic beta cell function and/or wherein the remission of the metabolic disorder, preferably diabetic remission, is achieved and/or maintained.

18 Claims, 15 Drawing Sheets

(56) References Cited

U.S. PATENT DOCUMENTS

| | | | |
|---|---|---|---|
| 2012/0237593 | A1 | 9/2012 | Comiskey et al. |
| 2012/0277175 | A1 | 11/2012 | Neto et al. |
| 2014/0031540 | A1* | 1/2014 | Eckhardt ............... C07H 15/26 536/55 |
| 2015/0272977 | A1 | 10/2015 | Reiche et al. |
| 2016/0361289 | A1 | 12/2016 | Kley et al. |
| 2017/0056366 | A1 | 3/2017 | Weiler et al. |
| 2017/0071969 | A1 | 3/2017 | Reiche |
| 2017/0239281 | A1 | 8/2017 | Reiche et al. |

FOREIGN PATENT DOCUMENTS

| | | | |
|---|---|---|---|
| EP | 2368552 A1 | 9/2011 | |
| WO | 0127128 A1 | 4/2001 | |
| WO | 2002083066 A2 | 10/2002 | |
| WO | 2004063209 A2 | 7/2004 | |
| WO | 2007093610 A1 | 8/2007 | |
| WO | 2007128749 A1 | 11/2007 | |
| WO | 2007129053 A1 | 11/2007 | |
| WO | WO2007/128749 | * 11/2007 | ........... C07D 309/10 |
| WO | 2008002824 A1 | 1/2008 | |
| WO | 2008042688 A2 | 4/2008 | |
| WO | 2008116179 A1 | 9/2008 | |
| WO | 2009124755 A1 | 10/2009 | |
| WO | 2009143020 A1 | 11/2009 | |
| WO | 2010022313 A2 | 2/2010 | |
| WO | 2010023594 A1 | 3/2010 | |
| WO | 2010048358 A2 | 4/2010 | |
| WO | 2010092125 A1 | 8/2010 | |
| WO | 2010092123 A8 | 6/2011 | |
| WO | WO2011/117295 | * 9/2011 | ......... A61K 31/4535 |
| WO | 2011153712 A1 | 12/2011 | |
| WO | 2012062698 A1 | 5/2012 | |
| WO | 2012140597 A1 | 10/2012 | |
| WO | 2013040164 A1 | 3/2013 | |
| WO | 2014016381 A1 | 1/2014 | |
| WO | 2014068007 A1 | 5/2014 | |
| WO | 2015091313 A1 | 6/2015 | |
| WO | 2015110402 A1 | 7/2015 | |
| WO | 2015150299 A2 | 10/2015 | |
| WO | 2016046150 A1 | 3/2016 | |
| WO | 2017032799 A1 | 3/2017 | |

OTHER PUBLICATIONS

"The use in animals of drugs licensed for human use only", chapter 46 of Comparative Veterinary Pharmacology, Toxicology and Therapy, edited by A. S. J. P. A. M. Van Miert © MTP Press Limited pp. 489-500 (Year: 1986).*
Michael H. Court, "Feline drug metabolism and disposition: pharmacokinetic evidence for species differences and molecular mechanisms" Vet Clin North Am Small Anim Pract. Sep.; 43(5): pp. 1-20 (Year: 2013).*
Henson et al., "Feline Models of Type 2 Diabetes Mellitus" ILAR Journal vol. 47 No. 3 pp. 234-242 (Year: 2006).*
Tirmenstein et al., "Nonclinical Toxicology Assessments Support the Chronic Safety of Dapagliflozin, a First-in-Class Sodium-Glucose Cotransporter 2 Inhibitor". International Journal of Toxicology, vol. 32, No. 5, 2013, pp. 336-350.
Xu et al., "Design, Synthesis, and Biological Evaluation of Deuterated C-Aryl Glycoside as a Potent and Long-Acting Renal Sodium-Dependent Glucose Cotransporter 2 Inhibitor for the Treatment of Type 2 Diabetes". Journal of Medicinal Chemistry, vol. 57, 2014, pp. 1236-1251.
Gehlen et al., "Comparison of Insulin and Glucose Metabolism in Horses with Pituitary Pars Intermedia Dysfunction Treated Versus Not Treated with Pergolide". Journal of Equine Veterinary Science, vol. 34, 2014, pp. 508-513.
Hirayama et al., Common mechanisms of inhibition for the Na+/glucose (hSGLT1) and Na+/C1-GABA (HGAT1) contransporters). British Journal of Pharmacology, vol. 134, Oct. 2001, pp. 484-495.

Frank et al., "Equine Metabolic Syndrome", ACVIM Consensus Statement, Journal of Veterinary Internal Medicine, vol. 24, No. 3, 2010, pp. 467-475.
International Search Report and Written Opinion for PCT/EP2014/077677 dated Jun. 9, 2015.
Deshpande et al., "A Practical Stereoselective Synthesis and Novel Cocrystallizations of an Amphiphatic SGLT-2 Inhibitor". Organic Process Research & Development, vol. 16, 2012, pp. 577-585.
Osto et al., "Diabetes from humans to cats". General and Comparative Endocrinology, vol. 182, 2013, pp. 48-53.
Rand, Jacquie S., "Pathogenesis of Feline Diabetes". Veterinary Clinics of North America, vol. 43, 2013, pp. 221-231.
Kakinuma et al., "(1S)-1,5-Anhydro-1-[5-(4-ethoxybenzyl)-2-methoxy-4-methylphenyl]-1-thio-d-glucitol (TS-071) is a Potent, Selective Sodium-Dependent Glucose Cotransporter 2 (SGLT2) Inhibitor for Type 2 Diabetes Treatment". Journal of Medicinal Chemistry, vol. 53, No. 8, 2010, pp. 3247-3261.
Sinha et al., "Pioglitazone—Do we really need it to manage type 2 diabetes?", Diabetes & Metabolic Syndrome: Clinical Reserach & Review, 7 (2013) pp. 52-55.
Durham et al., "type 2 diabetes mellitus with pancreatic B cell dysfunction in 3 horses confirmed with minimal model analysis", Equine Veterinary Journal (2009) 41 (9) pp. 924-929.
Ciobotaru, Emilia, "Diabetes Mellitus—Insights and Perspectives", Editor: Oluwafemi O. Oguntibeju, ISBN 978-953-51-0939-6, Jan. 2, 2013, Chapter 15, Spontaneous Diabetes Mellitus in Animals, pp. 271-296.
Yamamoto et al., "TS-071 is a novel, potent and selective renal sodium-glucose cotransporter 2 (SGLT2) inhibitor with anti-hyperglycaemic activity." British Journal of Pharmacology, vol. 164, No. 1, 2011, pp. 181-191.
Katsuno et al., "Sergliflozin, a Novel Selective Inhibitor of Low-Affinity Sodium Glucose Cotransporter (SGLT2), Validates the Critical Role of SGLT2 in Renal Glucose Reabsorption and Modulates Plasma Glucose Level." The Journal of Pharmacology and Experimental Therapeutics, vol. 320, No. 1, 2007, pp. 323-330.
Jeta et al., "Reduction of Renal Transport Maximum for Glucose by Inhibition of Na+-Glucose Cotransporter Suppresses Blood Glucose Elevation in Dogs." Biological and Pharmaceutical Bulletin, vol. 29, No. 1, 2006, pp. 114-118.
Grempler et al., "Empagliflozin, a novel selective sodium glucose cotransporter-2 (SGLT-2) inhibitor: characterisation and comparison with other SGLT-2 inhibitors." Diabetes, Obesity and Metabolism, vol. 14, 2012, pp. 83-90.
Sugimoto et al., "Novel Therapeutic Agents for the Treatment of Diabetes Sodium-Glucose Co-Transporter (SGLT) 2 Inhibitors." Cutting-Edge of Medicine, vol. 102, No. 6, 2013, pp. 1474-1483.
Diabetes, vol. 56, Suppl.1, 2007, pp. A144-A145.
Washburn, William N., "Evolution of sodium glucose co-transporter 2 inhibitors as anti-diabetic agents." Expert Opinion on Therapeutic Patients, vol. 19, No. 11, 2009, pp. 1485-1499.
Johnson et al., "Medical Implications of Obesity in Horses—Lessons for Human Obesity." Journal of Diabetes Science and Technology, vol. 3, No. 1, Jan. 2009, pp. 164-174.
French et al., "Pharmacokinetics and metabolic effects of triamcinolone anetonide and their possible relationships to glucocorticoid-induced laminitis in horses." Journal of Veterinary Pharmacology and Therapeutics, vol. 23, 2000, pp. 287-292.
Treiber et al., "Laminitis in Ponies is a Diabetic-like State" Experimental Biology, The FASEB Journal, Meeting Abstracts, vol. 21, No. 6, Abstract No. 737.23, Apr. 2007, p. A833. [Accessed at https://www.fasebj.org/doi/10.1096/fasebj.21.6.A833 on Apr. 17, 2018].
Osto et al., Diabetes from Humans to Cats, General and Comparative Endocrinology 182 (2013), pp. 48-53.
Mahmood, Application of Allometric Principles for the Prediction of Pharmacokinetics in Human and Veterinary Drug Development, Advanced Drug Delivery Reviews 59 (2007), pp. 1177-1192.
Terami et al., Long-Term Treatment with the Sodium Glucose Cotransporter 2 Inhibitor, Dapagliflozin, Ameliorates Glucose Homeostasis and Diabetic Nephropathy in db / db Mice , PLOSone Jun. 2014, 9(6) e100777, pp. 1-13.

(56) References Cited

OTHER PUBLICATIONS

Van Raalte et al., Improving glycaemic control in type 2 diabetes: Stimulate insulin secretion or provide beta-cell rest?, Diabetes Obes Metab. 2017;19: pp. 1205-1213.
Burchell et al. "Safety and efficacy of dapagliflozin, a novel antidiabetic drug, in healthy cats"; Abstract; JVIM, 32:588, 2018; 1 page.
O'Brien et al., "Immunohistochemical morphometry of pancreatic endocrine cells in diabetic, normoglycemic glucose-intolerant and normal cats"; J Comp Pathol, vol. 96, 1986, pp. 357-369.

* cited by examiner

TREATMENT OF METABOLIC DISORDERS IN FELINE ANIMALS

FIELD OF THE INVENTION

The present invention relates to veterinary medicine, in particular to the treatment and/or prevention of metabolic disorders in feline animals.

BACKGROUND OF THE INVENTION

Feline animals, e.g. cats, are affected by various metabolic disorders. A number of metabolic disorders are known in feline animals, including hyperglycemia, insulin resistance, diabetes (such as diabetes mellitus type 1 or type 2, or pre-diabetes), hepatic lipidosis, obesity, hyperinsulinemia, impaired glucose tolerance, ketosis (in particular ketoacidosis), dyslipidemia, dysadipokinemia, obesity, subclinical inflammation or systemic inflammation, in particular low grade systemic inflammation, which also comprises adipose tissue, Syndrome X (metabolic syndrome), atherosclerosis and/or inflammation of the pancreas. Various correlations exist amongst these disorders. Among these disorders, in the cat, diabetes, in particular pre-diabetes and diabetes mellitus type 2, as well as hyperglycemia, insulin resistance, hepatic lipidosis, and obesity are gaining more and more importance. This can at least partially be ascribed to changing living and feeding behavior of companion animals during the last years.

Diabetes mellitus is characterized by disturbances in carbohydrate, protein and triglyceride metabolism based on a relative or absolute lack of insulin. It is a relatively common endocrinopathy in feline animals like the cat. The incidence for cats has increased about 5 to 12 fold in the last four decades to approximately 0.5 to 1.2%. Several risk factors have been identified: age, obesity, neutering and gender. Male, castrated, obese and old (>10 years) cats have probably the greatest risk to develop diabetes mellitus.

The current classification divides diabetes mellitus into three classes:
(1.) Type 1 which results from the loss of function of insulin secreting cells, e.g. by immunologic destruction of beta cells or insulin auto-antibodies (juvenile diabetes in humans);
(2.) Type 2 which results from a failure of the insulin stimulated cells to respond properly to insulin stimuli; it is also associated to e.g. amyloid accumulation in beta cells; type 2 usually develops during a long time of the so called pre-diabetes state; and
(3.) Secondary diabetes mellitus which can due to diabetogenic drugs (e.g. long-acting glucosteroids, megestrol acetat, etc.) or to other primary diseases like pancreatitis, pancreas adenocarcinoma, cushing, hypo- or hyperthyroidism, growth-hormone producing tumors resulting in acromegaly.

In particular diabetes mellitus of type 2 is a growing problem for cat populations around the developed world. The lifestyle changes of cat owners are mirrored in their cats—increasingly they are kept indoors, with reduced activity levels, and fed a calorie-rich diet, leading to obesity and predisposition to diabetes mellitus type 2. As these trends continue, the incidence of diabetes mellitus in cats is sure to rise accordingly.

For the treatment of diabetes in humans, especially of type 2 diabetes mellitus, several oral antihyperglycemic drugs are approved. These drugs act e.g. by stimulating pancreatic insulin secretion in a glucose-independent or glucose-dependent manner (sulfonylurea/meglitinides, or DPP IV inhibitors, respectively), by enhancing tissue sensitivity to insulin (biguanides, thiazolidinediones), or by slowing postprandial intestinal glucose absorption (alpha-glucosidase inhibitors).

Other approaches have been contemplated for treating diabetes and reduce hyperglycemia in humans, including inhibition of the renal sodium-dependent glucose cotransporter SGLT2. SGLT2 in the kidney regulates glucose levels by mediating the reabsorption of glucose back into the plasma following filtration of the blood. SGLT2 inhibition thus induces glucosuria and may reduce blood glucose levels. For example, compound 1-cyano-2-(4-cyclopropylbenzyl)-4-(ß-D-glucopyranos-1-yl)-benzene is described as an SGLT2 inhibitor in WO 2007/128749. A large variety of further SGLT2 inhibitors are also known. In WO 2011/117295, which is concerned with the medication of predominantly carnivorous non-human animals with dipeptidyl peptidase IV (DPP-IV) inhibitors, various SGLT2 inhibitors are recited amongst numerous other types of compounds in the context of combination therapies with DPP-IV inhibitors.

SGLT2 inhibition has not previously been contemplated for treatment of metabolic disorders in feline animals, such as cats. In feline animals, medications for metabolic disorders are far less advanced than in humans. Unfortunately, even if a treatment or prophylaxis is effective in humans, e.g., or other non-feline animals, it is not possible to conclude that the same approach will also be effective, safe and otherwise appropriate in a feline animal, such as a cat.

Feline animals differ significantly from humans or, e.g., dogs in respect of their metabolisms.

Being strict carnivores, felines are not well adapted to carbohydrates in the diet. For example feline livers show no activities of glucokinase (Tanaka et al., Vet Res Commun. 2005, 29(6):477-485). In most mammals, e.g. dogs or humans, hepatic glucokinase acts as a "glucose sensor" that permits hepatic metabolism to respond appropriately to changes in plasma glucose concentrations. Additionally, the release of insulin from a cat's pancreas appears to be less responsive to glucose as a stimulus as compared to most other species (Curry et al., Comp Biochem Physiol. 1982. 72A (2): 333-338).

Another adaptation to a strictly carnivorous diet relates to the utilization of protein and fat for energy production—i.e. gluconeogenesis. In an omnivore, gluconeogenesis occurs primarily in starvation situations. In contrast, in an obligate carnivore, such as the cat, gluconeogenesis appears to be constantly active in the liver, regardless of nutritional status and be postprandially even higher than in a fasted state (Hoenig et al. Am J Physiol, 2011, 301(6):R1798-1807, Verbrugghe et al., Crit Rev Food Sci Nutr. 2012; 52(2):172-182).

Consequently, the pathophysiology of feline metabolic disorders, and thus also their responses to medication of such disorders differs from other species.

As a diabetic complication e.g. vision problems and cataracts are commonly seen with diabetes mellitus in dogs, but are rarely found in feline animals.

Oral medications for diabetes that are known from human medicine such as glipizide (sulfonylurea) work in some small proportion of cats, but these drugs may be completely ineffective if the pancreas is not working. Worse, in some studies glipizide and other oral hypoglycemic drugs have been shown to generate side effects such as vomiting and icterus and to damage the pancreas even further leading to a reduction of the chances of remission from diabetes for cats. They have also been shown to cause liver damage.

Even lower efficacies are reported for the other compound groups, i.e. meglitinides, biguanides, thiazolidinediones and α-glucosidase inhibitors (Palm C A et al., Vet Clin Small Anim 2013, 43: 407-415).

The gold-standard treatment of diabetic cats is currently considered to be injection of insulin. However, cats are notoriously unpredictable in their response to exogenous insulin. No single type of insulin is routinely effective in maintaining control of glycemia, even with twice-daily administration. Even with strict compliance from the owner control is often poor and secondary problems are common. Many owners find it impossible to achieve acceptable levels of compliance, as synchronization of food intake and insulin injection is impossible in the majority of cases. Ultimately many cats with diabetes mellitus are euthanized because of the disease.

The factors governing patient and owner compliance are also very different. In cats, oral administration, e.g., is yet more highly desirable than in humans.

A treatment that would allow better compliance and therefore better glycemic control than current insulin-based treatments would help to attenuate the progression of the disease and delay or prevent onset of complications in many animals.

Moreover, even when diabetic cats are treated aggressively with insulin and clinical remission is attained, this also does not necessarily normalize insulin secretion, pancreatic beta cell function and/or insulin resistance. Cats remain prone to a new onset of diabetes. It would be desirable to have a treatment of diabetes in feline animals which better improves, e.g., insulin resistance and pancreatic beta cell function (Reusch C E et al., Schweizer Archiv fuer Tierheilkunde 2011, 153811): 495-500).

Thus, there remains a particular need for effective, safe and otherwise appropriate treatments of metabolic disorders, including diabetes, in feline animals.

DISCLOSURE OF THE INVENTION

Summary of the Invention

The present inventors have surprisingly found that inhibition of SGLT2 is effective and safe in the treatment and/or prevention of metabolic disorders in feline animals.

The present invention thus provides the use of one or more SGLT2 inhibitors or a pharmaceutically acceptable form thereof in the treatment and/or prevention of a metabolic disorder of a feline animal.

Further, the present invention provides the use of one or more SGLT2 inhibitors or a pharmaceutically acceptable form thereof in the treatment and/or prevention of a metabolic disorder of a feline animal, wherein the one or more SGLT2 inhibitors is 1-cyano-2-(4-cyclopropyl-benzyl)-4-(β-D-glucopyranos-1-yl)-benzene (which is referred to in the following as compound A) or a pharmaceutically acceptable form thereof.

Compound A has the following chemical formula:

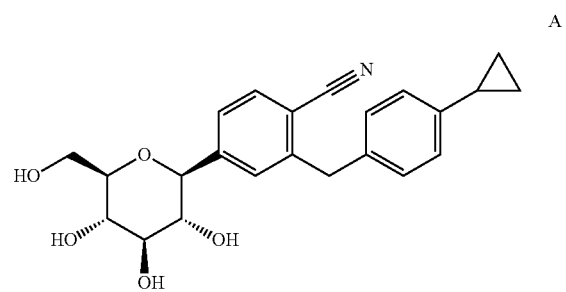 [SMILES: N#Cc1ccc([C@@H]2O[C@H](CO)[C@@H](O)[C@H](O)[C@H]2O)cc1Cc1ccc(C2CC2)cc1]

Further aspects of the invention are defined below as well as in the claims.

The pharmaceutically acceptable form of the one or more SGLT2 inhibitors, preferably compound A, may be a crystalline complex between the one or more SGLT2 inhibitors and one or more amino acids, such as proline.

According to the invention, the one or more SGLT2 inhibitors, preferably compound A, or pharmaceutically acceptable form thereof may be provided, e.g., for oral or parenteral administration, preferably for oral administration.

The one or more SGLT2 inhibitors, preferably compound A, or a pharmaceutically acceptable form thereof may be administered in dosages of 0.1 to 3.0 mg/kg body weight per day, preferably from 0.2 to 2.0 mg/body weight per day, more preferably from 0.1 to 1 mg/body weight per day. Thus, the one or more SGLT2 inhibitors, preferably compound A, or pharmaceutically acceptable form thereof may be prepared for the administration of 0.1 to 3.0 mg/kg body weight per day, preferably from 0.2 to 2.0 mg/kg body weight per day, more preferably from 0.1 to 1 mg/kg body weight per day.

The one or more SGLT2 inhibitors, preferably compound A, or pharmaceutically acceptable form thereof is preferably administered only once per day.

The present invention also provides a pharmaceutical composition comprising one or more SGLT2 inhibitors, preferably compound A, or a pharmaceutically acceptable form thereof, for use according to the invention as disclosed herein.

In the examples provided herein, therapeutic and/or prophylactic benefits resulting from inhibition of SGLT2 according to the present invention are demonstrated experimentally. Experimental data disclosed herein are intended to illustrate the invention, but not to have any limiting effect upon the scope of protection, which is defined herein below by the claims.

In particular, the present inventors have surprisingly found that the use of one or more SGLT2 inhibitors, preferably compound A, according to the present invention advantageously leads to a reduction in insulin resistance in treated, insulin resistant feline animals. That is, equivalently, the use of one or more SGLT2 inhibitors, preferably compound A, according to the present invention advantageously leads to increased insulin sensitivity in treated, insulin resistant feline animals. Insulin sensitivity may be calculated by a variety of surrogate indices e.g. during a glucose challenge as modified Belfiore Index (1/log(ΔΔUC-glucose*ΔΔUC-insulin)).

The invention thus allows improved treatment and/or prevention of diabetes, in particular of diabetes mellitus type 2, in feline animals.

The use of one or more SGLT2 inhibitors, preferably compound A, according to the present invention advantageously leads to a reduced insulin excursion, e.g. as measured during an intravenous glucose tolerance test (ivGTT), or after any other form of glucose intake, e.g. after a high-carbohydrate meal (postprandial insulin excursion) or after a stress induced elevation of blood glucose. More specifically, the use of one or more SGLT2 inhibitors, preferably compound A, according to the invention advantageously also leads to reduced second phase insulin secretion, e.g. as measured during an ivGTT, or after any other form of glucose intake, e.g. after a meal.

The use of one or more SGLT2 inhibitors, preferably compound A, according to the present invention advantageously also leads to a reduction in plasma levels of non-esterified fatty acids, or an improved elimination of non-esterified fatty acids from the bloodstream, e.g. as measured during an ivGTT, or after any other form of test elevating blood insulin.

The use of one or more SGLT2 inhibitors, preferably compound A, according to the present invention thus generally leads to improved glucose tolerance, i.e. reduces glucose intolerance.

The glucose excursion in an intravenous insulin tolerance test (ivITT) of a feline animal treated in accordance with the invention is, advantageously, also improved in comparison to an untreated animal.

The use of one or more SGLT2 inhibitors, preferably compound A, according to the present invention advantageously also leads to a reduction in body fat, blood leptin levels, and/or the respiratory exchange ratio (RER). The invention is also associated with anti-obesity effects, and may in particular advantageously prevent weight gain and/or lead to a decrease in body mass in a feline animal. In one aspect, the invention thus allows obesity and/or obesity-related metabolic disorders to be managed in a feline animal.

The effects of the uses according to the present invention (i.e. the above-mentioned beneficial effects upon insulin resistance/sensitivity, insulin excursion, second phase insulin secretion, glucose tolerance, elimination of non-esterified fatty acids, body fat, blood leptin levels, RER values and/or body mass) are also advantageous in that they allow for subclinical treatment, e.g. treatment of the pre-diabetes state in feline animals. They thus allow the possibility of preventing or delaying the onset of diabetes mellitus in feline animals. More particularly, they allow the possibility of preventing or delaying progression of certain metabolic disorders, symptoms or conditions as described herein (such as hyperglycemia, impaired glucose tolerance, insulin resistance, abnormal insulin excursion or glucose excursion, high levels of blood non-esterified fatty acids or leptin, obesity and/or pancreatic beta cell loss) into diabetes mellitus, in particular diabetes mellitus type 2, in feline animals.

A further advantage of the present invention is that the use of one or more SGLT2 inhibitors, preferably compound A, is effective against the metabolic disorders alone, i.e., if desired the use of one or more SGLT2 inhibitors, preferably compound A, in a feline animal provides a monotherapy (i.e. a stand-alone therapy; i.e., no other medication is administered to the feline animal for the treatment or prevention of the same metabolic disorder). The invention also allows for the possibility of combination therapy with another drug (e.g. a further insulin sensitizing drug or insulin itself).

A further advantage of the present invention is that, surprisingly, the use of one or more SGLT2 inhibitors, preferably compound A, is effective against the metabolic disorders alone, i.e., if desired the use of one or more SGLT2 inhibitors, preferably compound A, in a feline animal provides a monotherapy (i.e. a stand-alone therapy; i.e., no other medication is administered to the feline animal for the treatment or prevention of the same metabolic disorder). The invention also allows for the possibility of replacing insulin therapy in feline animals, or for combination therapy with insulin or another drug (e.g. a hypoglycemic drug). Such a combination advantageously leads to a decrease in the dose and/or frequency at which the insulin or other drug (e.g., hypoglycemic drug) is administered, compared to monotherapy of the feline animal with insulin or the other drug. Most advantageously, the feline animal may be weaned off insulin or the other drug. Thus, clinical remission is attained.

Thus, use of one or more SGLT2 inhibitors, preferably compound A, according to the present invention, provides improved treatment and/or prevention of metabolic diseases as disclosed herein, including diabetes and/or pre-diabetes, in feline animals.

The effects of using one or more SGLT2 inhibitors, preferably compound A, according to the present invention (e.g. the above-mentioned beneficial effects upon insulin resistance/sensitivity, insulin excursion, second phase insulin secretion, glucose tolerance, elimination of non-esterified fatty acids, body fat, blood leptin levels, RER values, body mass and/or hyperglycemia) may be relative to the same or a comparable feline animal prior to administration of one or more SGLT2 inhibitors, preferably compound A, according to the present invention, and/or relative to a comparable feline animal that has not received said treatment (e.g. a placebo group). In either case, when a comparison is made, the comparison may be made after a certain treatment period, e.g., 1, 2, 3, 4, 5, 6 or 7 days; 10 days, 14 days; 2, 3, 4, 5, 6, 7 or 8 weeks; 1, 2, 3 or 4 months. Preferably the treatment period is 4 weeks. Alternatively, the treatment period may be 6 or 8 weeks. Alternatively, the treatment period may be 8 weeks or more, e.g. 8-16 weeks.

A further advantage of the present invention is that one or more SGLT2 inhibitors, preferably compound A, may effectively be administered to a feline animal orally. Moreover, the one or more SGLT2 inhibitors, preferably compound A, according to the present invention can be administered only once per day. These advantages allow for better compliance of the treated feline animal and the owner. This leads to better glycemic controls of disorders (e.g. diabetes) for which feline animals are currently treated with insulin. Generally, the use of one or more SGLT2 inhibitors, preferably compound A, according to the present invention thus helps to attenuate (i.e. delays or prevents) the progression of metabolic disorders and delays or prevents the onset of metabolic disorders (e.g. diabetes) and their complications in feline animals.

Accordingly, the present invention also provides pharmaceutical compositions comprising one or more SGLT2 inhibitors, preferably compound A, according to the invention for use in treating and/or preventing metabolic disorders in feline animals.

The invention also provides methods of treating and/or preventing metabolic disorders in feline animals, comprising administering to a feline animal in need of such treatment and/or prevention an effective dose of one or more SGLT2 inhibitors, preferably compound A, as described herein.

Advantageously, the use of one or more SGLT2 inhibitors, preferably compound A, according to the present invention does not cause hypoglycemia.

The effects of using one or more SGLT2 inhibitors, preferably compound A, according to the present invention (e.g. the above-mentioned beneficial effects upon insulin resistance/sensitivity, insulin excursion, second phase insulin secretion, glucose tolerance, elimination of non-esterified fatty acids, body fat, blood leptin levels, RER values, body mass and/or hyperglycemia) may be relative to the same or a comparable feline animal prior to administration of the one or more SGLT2 inhibitors, preferably compound A, according to the present invention, and/or relative to a comparable feline animal that has received e.g. standard insulin treatment (e.g. a control group) or has been untreated.

A further advantage of the present invention is that the one or more SGLT2 inhibitors, preferably compound A, may effectively be administered to a feline animal orally, e.g. in liquid form. Moreover, the one or more SGLT2 inhibitors, preferably compound A, according to the present invention can be administered only once per day. These advantages allow for optimal dosing and compliance of the treated feline animal and owner.

Generally, the use of one or more SGLT2 inhibitors, preferably compound A, according to the present invention may thus attenuate, delay or prevent the progression of a metabolic disorder, e.g. the metabolic disorders disclosed herein, or may delay or prevent the onset of metabolic disorders and their complications in feline animals.

Definitions

All values and concentrations presented herein are subject to inherent variations acceptable in biological science within an error of ±10%. The term "about" also refers to this acceptable variation.

Treatment effects disclosed herein (such as an improvement, reduction or delayed onset of a disorder, disease or condition, or the improvement, reduction, increase or delay of any effect, index, marker level or other parameter relating to a disorder, disease or condition) may be observed with a statistical significance of $p<0.05$, preferably $<0.01$.

When reference is made herein to a deviation (e.g. an increase, elevation, excess, prolongation, raise, reduction, decrease, improvement, delay, abnormal levels, or any other change, alteration or deviation with respect to a reference), the deviation may be, e.g., by 5% or more, particularly 10% or more, more particularly 15% or more, more particularly 20% or more, more particularly 30% or more, more particularly 40% or more, or more particularly 50% or more, with respect to the relevant reference value, unless otherwise stated. Typically, the deviation will be by at least 10%, i.e. 10% or more. The deviation may also be by 20%. The deviation may also be by 30%. The deviation may also be by 40%. The relevant reference value may be generated from a group of reference animals which are treated with placebo instead of the one or more SGLT2 inhibitors, preferably compound A, or are untreated.

Herein, an excursion, e.g. an insulin excursions or glucose excursion, designates a change in concentration or level in blood over time. The magnitude of excursions, e.g. insulin excursions or glucose excursions may be expressed as area-under-curve (AUC) values.

Herein, the terms "active substance" or "active ingredient" encompass one or more SGLT2 inhibitors, preferably compound A, or any pharmaceutically acceptable form thereof (e.g. a prodrug or a crystalline form), for use according to the invention. In the case of a combination with one or additional active compound, the terms "active ingredient" or "active substance" may also include the additional active compound.

Herein, the expression "associated with", in particular encompasses the expression "caused by".

Herein, ivGTT refers to an intravenous glucose tolerance test. In an ivGTT, 0.8 g dextrose per kg body mass may typically be employed.

Herein, ivITT refers to an intravenous insulin tolerance test. In an ivITT, 0.05 U insulin per kg body mass may typically be employed.

SGLT2 Inhibitors

SGLT2 inhibitors for use according to the invention include, but are not limited to, glucopyranosyl-substituted benzene derivatives, for example as described in WO 01/27128, WO 03/099836, WO 2005/092877, WO 2006/034489, WO 2006/064033, WO 2006/117359, WO 2006/117360, WO 2007/025943, WO 2007/028814, WO 2007/031548, WO 2007/093610, WO 2007/128749, WO 2008/049923, WO 2008/055870, WO 2008/055940, WO 2009/022020 or WO 2009/022008, all hereby incorporated by reference.

Moreover, the one or more SGLT2 inhibitors for use according to the invention may be selected from the group consisting of the following compounds or pharmaceutically acceptable forms thereof:

(1) a glucopyranosyl-substituted benzene derivative of the formula (1)

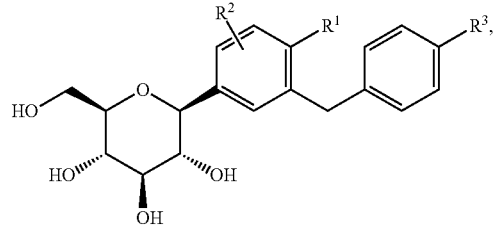

wherein $R^1$ denotes cyano, Cl or methyl (most preferably cyano);

$R^2$ denotes H, methyl, methoxy or hydroxy (most preferably H) and $R^3$ denotes cyclopropyl, hydrogen, fluorine, chlorine, bromine, iodine, methyl, ethyl, propyl, isopropyl, butyl, sec-butyl, iso-butyl, tert-butyl, 3-methyl-but-1-yl, cyclobutyl, cyclopentyl, cyclohexyl, 1-hydroxy-cyclopropyl, 1-hydroxy-cyclobutyl, 1-hydroxy-cyclopentyl, 1-hydroxy-cyclohexyl, ethinyl, ethoxy, difluoromethyl, trifluoromethyl, pentafluoroethyl, 2-hydroxyl-ethyl, hydroxymethyl, 3-hydroxypropyl, 2-hydroxy-2-methyl-prop-1-yl, 3-hydroxy-3-methyl-but-1-yl, 1-hydroxy-1-methyl-ethyl, 2,2,2-trifluoro-1-hydroxy-1-methyl-ethyl, 2,2,2-trifluoro-1-hydroxy-1-trifluoromethyl-ethyl, 2-methoxy-ethyl, 2-ethoxy-ethyl, hydroxy, difluoromethyloxy, trifluoromethyloxy, 2-methyloxy-ethyloxy, methylsulfanyl, methylsulfinyl, methlysulfonyl, ethylsulfinyl, ethylsulfonyl, trimethylsilyl, (R)-tetrahydrofuran-3-yloxy or (S)-tetrahydrofuran-3-yloxy or cyano;

wherein R3 is preferably selected from cyclopropyl, ethyl, ethinyl, ethoxy, (R)-tetrahydrofuran-3-yloxy or (S)-tetrahydrofuran-3-yloxy; and most preferably R3 is cyclopropyl, or a derivative thereof wherein one or more hydroxyl groups of the β-D-glucopyranosyl group are acylated with groups selected from $(C_{1-18}$-alkyl)carbonyl, $(C_{1-18}$-alkyl)oxycarbonyl, phenylcarbonyl and phenyl-$(C_{1-3}$-alkyl)-carbonyl;

(2) 1-cyano-2-(4-cyclopropyl-benzyl)-4-(β-D-glucopyranos-1-yl)-benzene, represented by formula (2):

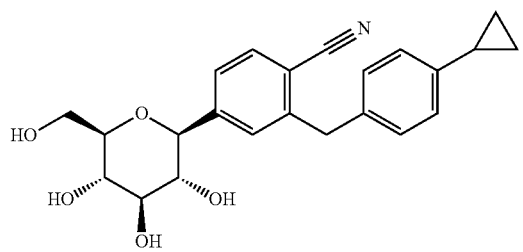 [SMILES: N#Cc1ccc([C@@H]2O[C@H](CO)[C@@H](O)[C@H](O)[C@H]2O)cc1Cc1ccc(C2CC2)cc1]

(3) Dapagliflozin, represented by formula (3):

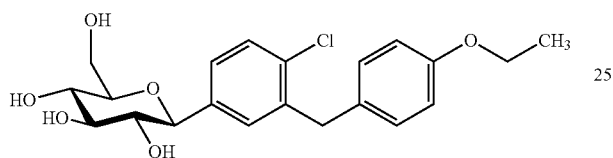

(4) Canagliflozin, represented by formula (4):

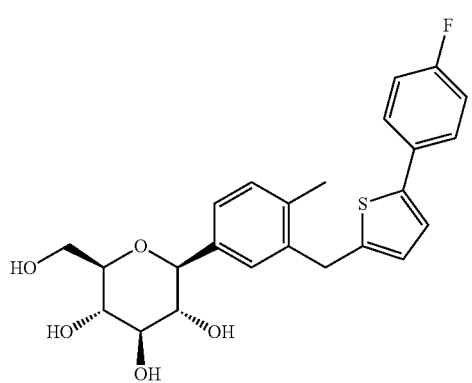 [SMILES: Cc1ccc([C@@H]2O[C@H](CO)[C@@H](O)[C@H](O)[C@H]2O)cc1Cc1ccc(-c2ccc(F)cc2)s1]

(5) Empagliflozin, represented by formula (5):

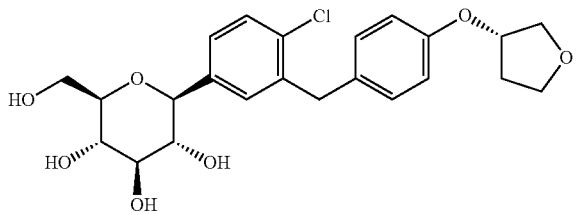 [SMILES: OC[C@H]1O[C@@H](c2ccc(Cl)c(Cc3ccc(O[C@H]4CCOC4)cc3)c2)[C@H](O)[C@@H](O)[C@@H]1O]

(6) Luseogliflozin, represented by formula (6):

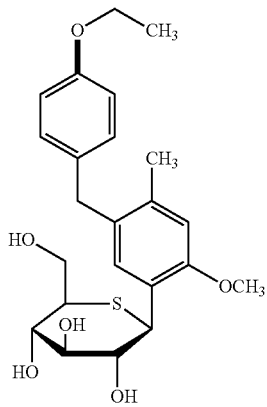

(7) Tofogliflozin, represented by formula (7):

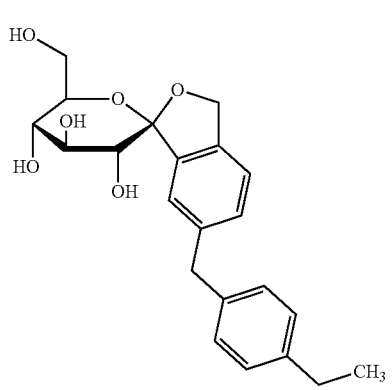

(8) Ipragliflozin, represented by formula (8):

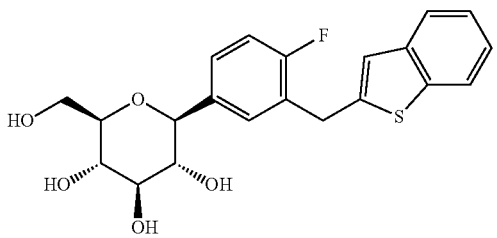 [SMILES: OC[C@H]1O[C@@H](c2ccc(F)c(Cc3cc4ccccc4s3)c2)[C@H](O)[C@@H](O)[C@@H]1O]

(9) Ertugliflozin, represented by formula (9):

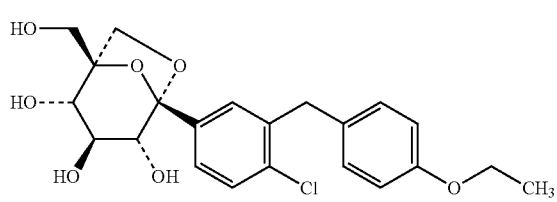 [SMILES: CCOc1ccc(Cc2cc([C@]34OC[C@](CO)(O3)[C@@H](O)[C@H](O)[C@H]4O)ccc2Cl)cc1]

(10) Atigliflozin, represented by formula (10):

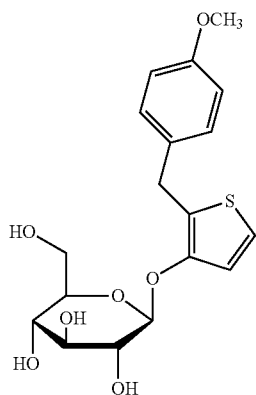

(11) Remogliflozin, represented by formula (11):

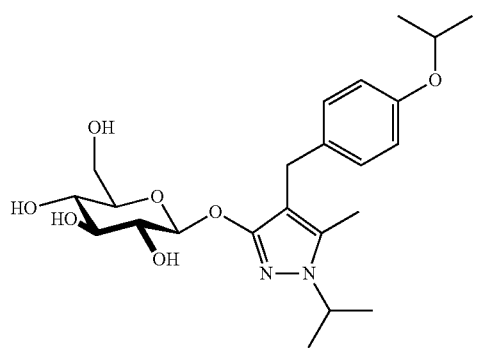

(12) a thiophene derivative of the formula (12)

(7-1)

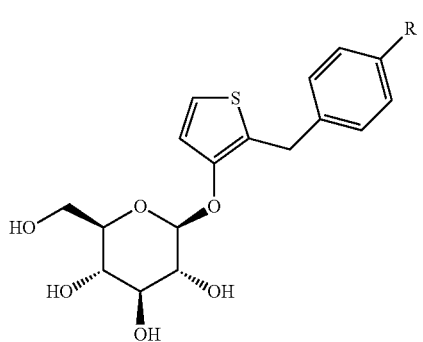

wherein R denotes methoxy or trifluoromethoxy;

(13) 1-(β-D-glucopyranosyl)-4-methyl-3-[5-(4-fluoro-phenyl)-2-thienylmethyl]benzene as described in WO 2005/012326, represented by formula (13);

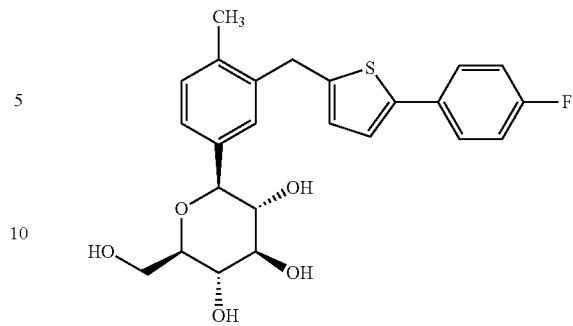

(14) a spiroketal derivative of the formula (14):

(9-1)

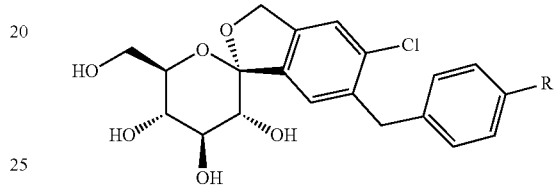

wherein R denotes methoxy, trifluoromethoxy, ethoxy, ethyl, isopropyl or tert. butyl;

(15) a pyrazole-O-glucoside derivative of the formula (15)

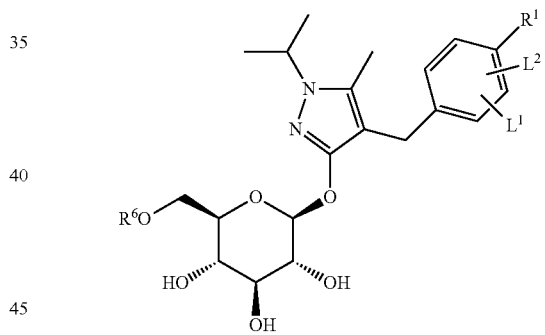

wherein
R$^1$ denotes C$_{1-3}$-alkoxy,
L$^1$, L$^2$ independently of each other denote H or F,
R$^6$ denotes H, (C$_{1-3}$-alkyl)carbonyl, (C$_{1-6}$-alkyl)oxy-carbonyl, phenyloxycarbonyl, benzyloxycarbonyl or benzylcarbonyl;

(16) a compound of the formula (16):

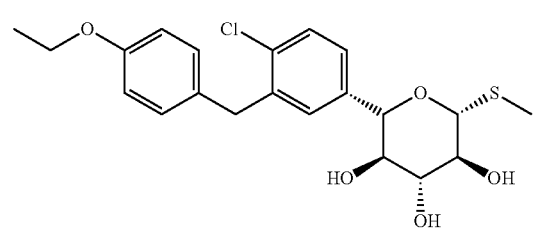

(17) and Sergliflozin, represented by formula (17):

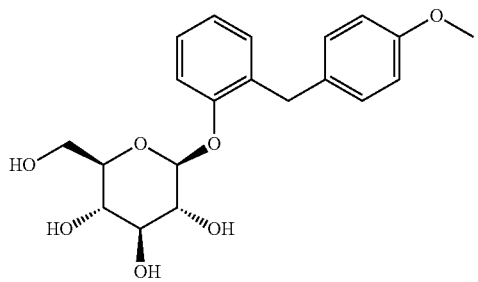 [SMILES: COc1ccc(Cc2ccccc2O[C@@H]2O[C@H](CO)[C@@H](O)[C@H](O)[C@H]2O)cc1]

The term "dapagliflozin" as employed herein refers to dapagliflozin of the above structure as well as pharmaceutically acceptable forms thereof, including hydrates and solvates thereof, and crystalline forms thereof. The compound and methods of its synthesis are described in WO 03/099836 for example. Preferred hydrates, solvates and crystalline forms are described in the patent applications WO 2008/116179 and WO 2008/002824 for example. These references hereby incorporated by reference.

The term "canagliflozin" as employed herein refers to canagliflozin of the above structure as well as pharmaceutically acceptable forms thereof, including hydrates and solvates thereof, and crystalline forms thereof. The compound and methods of its synthesis are described in WO 2005/012326 and WO 2009/035969 for example. Preferred hydrates, solvates and crystalline forms are described in the patent application WO 2008/069327 for example. These references hereby incorporated by reference.

The term "empagliflozin" as employed herein refers to empagliflozin of the above structure as well as pharmaceutically acceptable forms thereof, including hydrates and solvates thereof, and crystalline forms thereof. The compound and methods of its synthesis are described in WO 2005/092877, WO 2006/120208 and WO 2011/039108 for example. A preferred crystalline form is described in the patent applications WO 2006/117359 and WO 2011/039107 for example. These references hereby incorporated by reference.

The term "atigliflozin" as employed herein refers to atigliflozin of the above structure as well as pharmaceutically acceptable forms thereof, including hydrates and solvates thereof, and crystalline forms thereof. The compound and methods of its synthesis are described in WO 2004/007517 for example. These references hereby incorporated by reference. These references hereby incorporated by reference.

The term "ipragliflozin" as employed herein refers to ipragliflozin of the above structure as well as pharmaceutically acceptable forms thereof, including hydrates and solvates thereof, and crystalline forms thereof. The compound and methods of its synthesis are described in WO 2004/080990, WO 2005/012326 and WO 2007/114475 for example. These references hereby incorporated by reference.

The term "tofogliflozin" as employed herein refers to tofogliflozin of the above structure as well as pharmaceutically acceptable forms thereof, including hydrates and solvates thereof, and crystalline forms thereof. The compound and methods of its synthesis are described in WO 2007/140191 and WO 2008/013280 for example. These references hereby incorporated by reference.

The term "luseogliflozin" as employed herein refers to luseogliflozin of the above structure as well as pharmaceutically acceptable forms thereof, including hydrates and solvates thereof, and crystalline forms thereof.

The term "ertugliflozin" as employed herein refers to ertugliflozin of the above structure as well as pharmaceutically acceptable forms thereof, including hydrates and solvates thereof, and crystalline forms thereof. The compound is described for example in WO 2010/023594. These references hereby incorporated by reference.

The term "remogliflozin" as employed herein refers to remogliflozin of the above structure as well as pharmaceutically acceptable forms thereof, including prodrugs of remogliflozin, in particular remogliflozin etabonate, including hydrates and solvates thereof, and crystalline forms thereof. Methods of its synthesis are described in the patent applications EP 1 213 296 and EP 1 354 888 for example. These references hereby incorporated by reference.

The term "sergliflozin" as employed herein refers to sergliflozin of the above structure as well as pharmaceutically acceptable forms thereof, including prodrugs of sergliflozin, in particular sergliflozin etabonate, including hydrates and solvates thereof, and crystalline forms thereof. Methods for its manufacture are described in the patent applications EP 1 344 780 and EP 1 489 089 for example. These references hereby incorporated by reference.

The compound of formula (16) above and its manufacture are described for example in WO 2008/042688 or WO 2009/014970. These references hereby incorporated by reference.

Preferred SGLT2 inhibitors are glucopyranosyl-substituted benzene derivatives. Optionally, one or more hydroxyl groups of the glucopyranosyl group in such one or more SGLT2 inhibitors may be acylated with groups selected from ($C_{1-18}$-alkyl)carbonyl, ($C_{1-18}$-alkyl)oxycarbonyl, phenylcarbonyl and phenyl-($C_{1-3}$-alkyl)-carbonyl.

More preferred are glucopyranosyl-substituted benzonitrile derivatives of formula (1) as disclosed herein above. Yet more preferred are glucopyranosyl-substituted benzonitrile derivatives of formula (18):

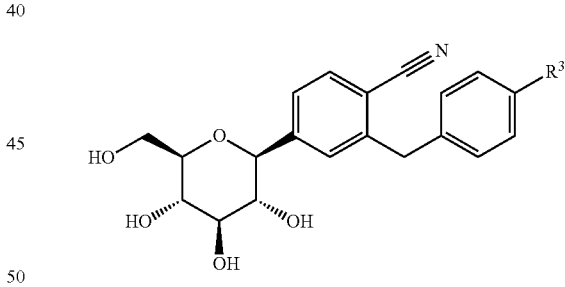

wherein R3 denotes cyclopropyl, hydrogen, fluorine, chlorine, bromine, iodine, methyl, ethyl, propyl, isopropyl, butyl, sec-butyl, iso-butyl, tert-butyl, 3-methyl-but-1-yl, cyclobutyl, cyclopentyl, cyclohexyl, 1-hydroxy-cyclopropyl, 1-hydroxy-cyclobutyl, 1-hydroxy-cyclopentyl, 1-hydroxy-cyclohexyl, ethinyl, ethoxy, difluoromethyl, trifluoromethyl, pentafluoroethyl, 2-hydroxyl-ethyl, hydroxymethyl, 3-hydroxy-propyl, 2-hydroxy-2-methyl-prop-1-yl, 3-hydroxy-3-methyl-but-1-yl, 1-hydroxy-1-methyl-ethyl, 2,2,2-trifluoro-1-hydroxy-1-methyl-ethyl, 2,2,2-trifluoro-1-hydroxy-1-trifluoromethyl-ethyl, 2-methoxy-ethyl, 2-ethoxy-ethyl, hydroxy, difluoromethyloxy, trifluoromethyloxy, 2-methyloxy-ethyloxy, methylsulfanyl, methylsulfinyl, methlysulfonyl, ethylsulfinyl, ethylsulfonyl, trimethylsilyl, (R)-tetrahydrofuran-3-yloxy or (S)-tetrahydrofuran-3-yloxy or cyano (wherein R3 is preferably selected from cyclopropyl, ethyl, ethinyl, ethoxy, (R)-tetrahydrofuran-3-yloxy or (S)-tetrahydrofuran-3-yloxy; and R3 most preferably is cyclopropyl, or a derivative thereof wherein one or more hydroxyl groups of the β-D-glucopyranosyl group are acylated with groups selected from (C1-18-alkyl)carbonyl, (C1-18-alkyl)oxycarbonyl, phenylcarbonyl and phenyl-(C1-3-alkyl)-carbonyl.

Preferably, such SGLT2 inhibitor is 1-cyano-2-(4-cyclopropyl-benzyl)-4-(β-D-glucopyranos-1-yl)-benzene as shown in formula (2) (also referred to herein as "compound A"). Optionally, one or more hydroxyl groups of the β-D-glucopyranosyl group of compound A may be acylated with groups selected from ($C_{1-18}$-alkyl)carbonyl, ($C_{1-18}$-alkyl)oxycarbonyl, phenylcarbonyl and phenyl-($C_{1-3}$-alkyl)-carbonyl.

Thus, in preferred embodiments, a SGLT2 inhibitor according to the present invention is a glucopyranosyl-substituted benzene derivative SGLT2 inhibitor, preferably a SGLT2 inhibitor of formula (1), more preferably of formula (18), or yet more preferably of formula (2) (i.e. compound A), in each case as defined herein above.

Metabolic Disorders

The metabolic disorder may be diabetes, pre-diabetes, obesity and/or any disorder, disease, condition or symptom associated with one or more of those disorders. In particular, the metabolic disorder may be hyperglycemia, insulin resistance, diabetes and/or hepatic lipidosis. Further relevant metabolic disorders include hyperinsulinemia, impaired glucose tolerance, ketosis (in particular ketoacidosis), hyperlipidemia, elevated blood levels of fatty acids and/or of glycerol, Syndrome X (metabolic syndrome), atherosclerosis, inflammation of the pancreas, inflammation of adipose tissue and/or loss of pancreatic beta cell function.

In some embodiments, the metabolic disorder is diabetes. Herein, diabetes may be pre-diabetes, diabetes mellitus type 1 or diabetes mellitus type 2. In particular, diabetes may be diabetes mellitus type 2. In some embodiments, diabetes may be associated with obesity.

In some embodiments, the metabolic disorder is hyperglycemia. Herein, hyperglycemia may be associated with diabetes, e.g. with diabetes mellitus type 2. In some embodiments, hyperglycemia may be associated with obesity. The hyperglycemia may be chronic.

In some embodiments, the metabolic disorder is insulin resistance. Herein, insulin resistance may be associated with diabetes, e.g. with diabetes mellitus type 2. In some embodiments, insulin resistance may be associated with obesity.

In some embodiments, the metabolic disorder is impaired glucose tolerance (IGT). Herein, impaired glucose tolerance may be associated with diabetes, e.g. with diabetes mellitus type 2. In some embodiments, impaired glucose tolerance may be associated with obesity.

In some embodiments, the metabolic disorder is hyperinsulinemia. Herein, hyperinsulinemia may be associated with diabetes, e.g. with diabetes mellitus type 2. In some embodiments, hyperinsulinemia may be associated with obesity.

In some embodiments, the metabolic disorder is one or more of hyperglycemia, insulin resistance, and hepatic lipidosis. In some embodiments, the metabolic disorder is selected from hyperglycemia and insulin resistance.

In some embodiments, the metabolic disorder is one or more of hyperinsulinemia, impaired glucose tolerance, hyperglycemia and insulin resistance.

In certain embodiments, the feline animal is obese. For example, according to the invention, one or more metabolic disorders selected from hyperglycemia, insulin resistance and hepatic lipidosis may be treated and/or prevented in an obese feline animal. Moreover, e.g., hyperinsulinemia and/or impaired glucose tolerance may be treated and/or prevented in an obese feline animal. Moreover, one or more disorders selected from ketosis (in particular ketoacidosis), hyperlipidemia, elevated blood levels of fatty acids and/or of glycerol, Syndrome X (metabolic syndrome), atherosclerosis, inflammation of the pancreas, inflammation of adipose tissue and loss of pancreatic beta cell function may be treated and/or prevented in an obese feline animal.

In certain embodiments, the feline animal is suffering from diabetes, e.g. from diabetes mellitus type 2. For example, according to the invention, one or more metabolic disorders selected from the group hyperglycemia, insulin resistance and hepatic lipidosis may be treated and/or prevented in a feline animal that is suffering from diabetes, e.g. from diabetes mellitus type 2. Moreover, e.g., hyperinsulinemia and/or impaired glucose tolerance may be treated and/or prevented in a feline animal that is suffering from diabetes, e.g. from diabetes mellitus type 2. Moreover, one or more disorders selected from ketosis (in particular ketoacidosis), hyperlipidemia, elevated blood levels of fatty acids and/or of glycerol, Syndrome X (metabolic syndrome), atherosclerosis, inflammation of the pancreas, inflammation of adipose tissue and loss of pancreatic beta cell function may be treated and/or prevented in a feline animal that is suffering from diabetes, e.g. from diabetes mellitus type 2.

In some embodiments, the feline animal is obese and is suffering from diabetes, e.g. from diabetes mellitus type 2. In some embodiments, the feline animal is suffering from diabetes, e.g. from diabetes mellitus type 2 but is not obese. In some embodiments, the feline animal is obese and not suffering from diabetes.

The present invention also provides the use of one or more SGLT2 inhibitors, preferably compound A, for treating and/or preventing the degeneration of pancreatic beta cells. For example by increasing pancreatic beta-cell mass, and/or improving and/or restoring the functionality (i.e. insulin secretion) of pancreatic beta cells in a feline animal.

Ketosis is a state of elevated levels of ketone bodies in the body. Ketoacidosis can be described as a type of metabolic acidosis which is caused by high concentrations of ketone bodies, formed by the breakdown of fatty acids and the deamination of amino acids. The two common ketones produced in humans are acetoacetic acid and β-hydroxybutyrate. In cats, predominantly three ketones are found: acetoacetic acid, beta-hydroxybutyrate and pyruvic acid. Ketoacidosis can be smelled on a subject's breath. This is due to acetone, a direct byproduct of the spontaneous decomposition of acetoacetic acid.

Ketoacidosis is an extreme and uncontrolled form of ketosis. Ketosis is also a normal response to prolonged fasting. In ketoacidosis, the body fails to adequately regulate ketone production, esp. by producing Acetyl-CoA, causing such a severe accumulation of keto acids that the pH of the blood is substantially decreased, i.e. the excess ketone bodies may significantly acidify the blood. In extreme cases ketoacidosis can be fatal.

Ketoacidosis may occur when the body is producing high levels of ketone bodies via the metabolism of fatty acids (ketosis) and insulin does not sufficiently slow this production (e.g. due to insulin resistance/reduced insulin sensitivity). The presence of high blood sugar levels (hyperglycemia) caused by the lack of insulin can lead to further acidity in the blood. In healthy individuals this normally does not occur because the pancreas produces insulin in response to rising ketone/blood sugar levels.

Ketoacidosis is most common in untreated diabetes mellitus, when the liver breaks down fat and proteins in response to a perceived need for respiratory substrate.

Pre-diabetes in feline animals is characterized by hyperinsulinemia, insulin resistance in target organs, impaired glucose tolerance incl. e.g. an altered insulin response to a glycemic challenge, e.g. also e.g. induced by stress. Pre-diabetes is also often associated with obesity. Pre-diabetes may also be associated with intermittent hyperglycemia.

Type 2 diabetes in feline animals is characterized by both reduced insulin production and insulin resistance in target organs. Reduced insulin production can e.g. be caused by amyloid accumulation in β-cells, glucose toxicity and/or pancreas infections. The defect in beta cell function is usually progressive, and in some feline animals results in complete loss of insulin secretion. Genetic factors, glucosteroids, progesterone, lack or exercise, and obesity are possible reasons for insulin resistance. For instance, in healthy cats, insulin sensitivity decreases by 50% after a weight gain of >40%. It is thought that diabetic cats have primarily type 2, based on the fact that most diabetic cats have islet amyloid, which has been called the hallmark of type 2 diabetes.

It is thought that only a substantial minority of cats have a secondary form of diabetes mellitus.

Clinical signs of diabetes mellitus observed with feline animals include polydipsia, polyuria, weight loss, and/or polyphagia. In cats anorexia is more often described as polyphagia. Pathognomonic for diabetes mellitus in cats is a plantigrade stance (weakness in hind legs, hocks touch the ground when the cat walks). This is caused by a diabetic neuropathy.

Further particularly relevant clinical signs of diabetes mellitus in feline animals within the context of the present invention are hyperglycemia and glucosuria. Hyperglycemia in a feline animal (e.g. a cat) is defined as plasma glucose values above normal values (3.9-8.3 mmol/l or 70-150 mg/dl), e.g. 8 mmol/l or more or 150 mg/dl or more plasma glucose. Glucosuria in a feline animal (e.g. a cat) is defined as glucose levels in urine above normal values (0-2 mmol/L, or 36 mg/dl). The renal threshold is reached with blood glucose concentrations of approximately 11-17 mmol/l or 200 to 300 mg/dl.

The diagnosis of diabetes mellitus in feline animals may alternatively be based on three criteria, e.g., as follows:
(1) Fasting blood glucose concentration measurements>250 mg/dl;
(2) Glucosuria as defined above; and
(3) One or more of the following: polyuria, polydipsia, polyphagia, weight loss despite good appetite, or ketonuria (without signs of severe ketoacidosis).

In addition to the above mentioned diagnostics and in order to support them, further examinations can include hematology, blood chemistry, x-ray and/or abdominal ultrasound.

Preferably, the use of the one or more SGLT2 inhibitors, preferably compound A, according to the invention allows normal or near-normal blood glucose concentrations to be maintained and/or established. However,—unlike for human therapy—this not believed to be always necessary for diabetic animals and therefore not always the goal of a treatment according to the invention. According to the invention, blood glucose concentrations may also be maintained, e.g., between 5.5 and 16.6 mmol/l or 100 to 300 mg/dl. For feline animals this will often be satisfactory.

A goal of the treatment of pre-diabetes or diabetes in feline animals according to the invention may be the elimination of owner-observed signs (e.g. lethargy, polyuria, polydipsia, weight loss, polyphagia, etc.) that occur secondary to hyperglycemia of untreated animals. Further treatment goals or treatment effects may be one or more of any of the advantageous effects of the invention disclosed herein, including but not limited to any one or more of improved glucose tolerance, increased insulin sensitivity, reduced insulin resistance, improved glucose excursion in an ivITT, improved insulin excursion in an ivGTT or an oral glucose tolerance test (OGTT), reduced second phase insulin secretion, reduced body fat, body mass, and/or blood leptin levels, a reduced respiratory exchange ratio (RER), and/or the absence of weight gain in case of an obese animal.

Diabetic remission is used in cats when normal (or close to normal) blood glucose concentrations are achieved, clinical signs have improved and insulin administration can be withdrawn or has not been employed for at least four consecutive weeks. However, viability of pancreatic beta-cells may not have fully recovered. The use of one or more SGLT2 inhibitors, preferably compound A, and thus the reduction of blood glucose concentrations and an improvement of insulin resistance and pancreatic beta cell function is putatively of crucial relevance to achieve and maintain remission of diabetes in a feline animal.

Insulin resistance can be described as the condition in which normal amounts of insulin are inadequate to produce a normal insulin response from fat, muscle and liver cells. Insulin resistance in fat cells reduces the effects of insulin and results in elevated hydrolysis of stored triglycerides in the absence of measures which either increase insulin sensitivity or which provide additional insulin. Increased mobilization of stored lipids in these cells elevates free fatty acids in the blood plasma. Insulin resistance in muscle cells reduces glucose uptake (and so local storage of glucose as glycogen), whereas insulin resistance in liver cells results in impaired glycogen synthesis and a failure to suppress glucose production. Elevated blood fatty acid levels, reduced muscle glucose uptake, and increased liver glucose production, may all contribute to elevated blood glucose levels (hyperglycemia).

Surrogate indices of insulin sensitivity may be calculated according to the QUICKI (quantitative insulin sensitivity check index: 1/log(glucose*insulin)) for basal blood level. For dynamic testing, e.g. during a glucose challenge a modified Belfiore Index (1/log(ΔΔUC-glucose*ΔΔUC-insulin)) can be employed.

Insulin resistance may be present in association with obesity, visceral adiposity, hypertension and dyslipidemia involving elevated triglycerides, small dense low-density lipoprotein (sdLDL) particles, and decreased HDL cholesterol levels. With respect to visceral adiposity, a great deal of evidence in humans suggests two strong links with insulin resistance. First, unlike subcutaneous adipose tissue, visceral adipose cells produce significant amounts of proinflammatory cytokines such as tumor necrosis factor-alpha (TNF-alpha), and Interleukins-1 and -6, etc. In numerous experimental models, these proinflammatory cytokines profoundly disrupt normal insulin action in fat and muscle cells, and may be a major factor in causing the whole-body insulin resistance observed in human patients with visceral adiposity. Similar, in felines excessive fat depots contribute to low grade systemic inflammation. The cause of the vast majority of cases of insulin resistance remains unknown. There is clearly an inherited component. However, there are some grounds for suspecting that insulin resistance is related to a high-carbohydrate diet. Inflammation also seems to be implicated in causing insulin resistance.

Hyperinsulinemia can be described as a condition in which there are excess levels, i.e., more than about 35 pmol/L under basal or about 200 pmol/L during e.g., a glycemic challenge (e.g. ivGTT or stress) of insulin circulating in the blood. As mentioned, it is commonly present in cases of, and may be a consequence of, insulin resistance in feline animals.

Impaired glucose tolerance can be described as condition in which the response to a after a glycemic challenge e.g. after a meal or after a loading test (glucose tolerance test) or after stress induced elevation of blood glucose concentration, the glycemic peak of the glucose excursion is higher and/or the duration of the glucose excursion is prolonged.

Dyslipidemia or hyperlipidemia is the presence of raised or abnormal levels of lipids and/or lipoproteins in the blood. Lipid and lipoprotein abnormalities are regarded as a highly modifiable risk factor for cardiovascular disease due to the influence of cholesterol. Glycerol is a precursor for the synthesis of triacylglycerols (triglycerides) and of phospholipids in the liver and adipose tissue. When the body uses stored fat as a source of energy, glycerol and fatty acids are released into the bloodstream after hydrolysis of the triglycerides. The glycerol component can be converted to glucose by the liver and provides energy for cellular metabolism. Normal levels of free fatty acids in the blood of companion (such as feline) animals are triglyceride concentrations of 50 to 100 mg/dl (0.6 to 1.2 mmol/l). Normal levels of blood cholesterol are, e.g., 70-150 mg/dl for the cat.

Dysadipokinemia can be described as a condition in which the circulating plasma levels of biologically active substances produced in adipose tissue that act in an autocrine/paracrine or endocrine fashion is deviated. e.g. an elevation of leptin and/or a reduction of adiponectin.

Subclinical inflammation or systemic inflammation, in particular low grade systemic inflammation is characterized by increased expression and secretion of pro-inflammatory cytokines such as tumor necrosis factor-alpha and/or lower expression and secretion of anti-inflammatory cytokines e.g. interleukin-10 and/or their respective receptors.

Obesity can be described as a medical condition in which excess body fat has accumulated to the extent that it may have an adverse effect on health, leading to reduced life expectancy. In obese felines e.g. a body condition score (BCS) of larger then 6 (out of 9) is encountered.

Metabolic disorders to be treated and/or prevented according to the invention include Syndrome X (metabolic syndrome). This disorder can be described as a combination of medical disorders that increase the risk of developing cardiovascular disease and diabetes. Metabolic syndrome is also known as metabolic Syndrome X (metabolic syndrome), Syndrome X (metabolic syndrome), insulin resistance syndrome, Reaven's syndrome, and CHAOS (as an abbreviation for Coronary artery disease, Hypertension, Atherosclerosis, Obesity, and Stroke).

The exact mechanisms of the complex pathways of metabolic syndrome are not yet completely known. The pathophysiology is extremely complex and has been only partially elucidated. Most patients are older, obese, sedentary, and have a degree of insulin resistance. The most important factors in order are: (1) overweight and obesity, (2) genetics, (3) aging, and (4) sedentary lifestyle, i.e., low physical activity and excess caloric intake.

A further risk factor is diabetes mellitus. At least in humans, the large majority (~75%) of patients with type 2 diabetes or impaired glucose tolerance (IGT) have metabolic syndrome.

The pathophysiology is commonly characterized by the development of visceral fat after which the adipocytes (fat cells) of the visceral fat increase plasma levels of TNF-alpha and alter levels of a number of other substances (e.g., adiponectin, resistin, PAI-1). TNF-alpha has been shown not only to cause the production of inflammatory cytokines, but possibly to trigger cell signaling by interaction with a TNF-alpha receptor that may lead to insulin resistance.

Current first line treatment is change of lifestyle (i.e., caloric restriction and physical activity). However, drug treatment is frequently required. Individual disorders contributing to metabolic syndrome may be treated separately. Diuretics and ACE inhibitors may be used to treat hypertension. Cholesterol drugs may be used to lower LDL cholesterol and triglyceride levels, if they are elevated, and to raise HDL levels if they are low. Such treatments may be combined with the use of one or more SGLT2 inhibitors, preferably compound A, according to the present invention.

Metabolic disorders to be treated and/or prevented according to the invention include inflammation of the pancreas (pancreatitis). This disorder may occur as either an acute form of a chronic form. Chronic pancreatitis may occur with or without steatorrhea and/or diabetes mellitus.

Pancreatitis may be caused by hypertriglyceridemia (in particular when triglyceride values exceed 1500 mg/dl (16 mmol/1), hypercalcemia, viral infection, trauma, vasculitis (i.e. inflammation of the small blood vessels within the pancreas), and autoimmune pancreatitis.

Metabolic disorders, especially dyslipidemia and elevated serum levels of triglycerides are risk factors for the development of pancreatitis, and may thus be treated according to the present invention in association with pancreatitis. Accordingly, the present invention also provides for prevention of pancreatitis. Accordingly, the present invention also provides for prevention of pancreatitis.

Metabolic disorders to be treated and/or prevented according to the invention include an inflammation of adipose tissue (panniculitis), which is a group of disorders characterized by inflammation of subcutaneous adipose tissue.

Panniculitis may occur in any fatty tissue (cutaneous and/or visceral). It may be diagnosed on the basis of a deep skin biopsy, and can be further classified by histological characteristics based on the location of the inflammatory cells (within fatty lobules or in the septa which separate them) and on the presence or absence of vasculitis. Panniculitis can also be classified based on the presence or absence of systemic symptoms.

Metabolic diseases, esp. pancreatitis, are risk factors for the development of panniculitis, and may thus be treated according to the present invention in association with panniculitis. Accordingly, the present invention also provides for prevention of panniculitis.

Feline Animals

Herein, a feline animal is a member of the Felidae family (i.e. a felid). It may thus belong either to the subfamily felinae or the subfamily pantherinae. The term feline animal encompasses the term cat, e.g., a domestic cat. The term domestic cat encompasses the terms *Felis catus* and *Felis silvestris catus*.

Pharmaceutically Acceptable Forms

Herein, references to SGLT2 inhibitors and/or their use according to the invention encompass pharmaceutically acceptable forms of the SGLT2 inhibitors, unless otherwise stated.

According to the invention, any pharmaceutically acceptable form of the SGLT2 inhibitor, e.g. of formula (1), preferably formula (18), more preferably formula (2), may be used. E.g. a crystalline form may be used. Prodrug forms are also encompassed by the present invention.

Prodrug forms may include, e.g., esters and/or hydrates. The term prodrug is also meant to include any covalently bonded carrier which releases the active compound of the invention in vivo when the prodrug is administered to a mammalian subject. Prodrugs of a compound of the invention may be prepared by modifying functional groups present in the compound of the invention in such a way that the modifications are cleaved, either in routine manipulation or in vivo, to the parent compound of the invention.

Crystalline forms for use according to the invention include a complex of an SGLT2 inhibitor with one or more amino acids (see e.g. WO 2014/016381). An amino acid for such use may be a natural amino acid. The amino acid may be a proteogenic amino acid (including L-hydroxyproline), or a non-proteogenic amino acid. The amino acid may be a D- or an L-amino acid. In some preferred embodiments the amino acid is proline (L-proline and/or D-proline, preferably L-proline). E.g., a crystalline complex of 1-cyano-2-(4-cyclopropyl-benzyl)-4-(β-D-glucopyranos-1-yl)-benzene (formula (2); compound A) with proline (e.g. L-proline) is preferred.

Thus, herein is disclosed a crystalline complex between one or more natural amino acids and an SGLT2 inhibitor, e.g., a crystalline complex between one or more natural amino acids and a glucopyranosyl-substituted benzene derivative SGLT2 inhibitor, preferably a SGLT2 inhibitor of formula (1), more preferably of formula (18) or yet more preferably of formula (2) (compound A). Thus, herein is disclosed a crystalline complex between one or more natural amino acids and 1-cyano-2-(4-cyclopropyl-benzyl)-4-(β-D-glucopyranos-1-yl)-benzene (compound A).

Further disclosed herein is the use of one or more crystalline complexes as defined hereinbefore or hereinafter for preparing a pharmaceutical composition which is suitable for the treatment and/or prevention of diseases or conditions which can be influenced by inhibiting sodium-dependent glucose co-transporter SGLT, preferably SGLT2. Further disclosed herein is the use of one or more crystalline complexes as defined hereinbefore or hereinafter for preparing a pharmaceutical composition for inhibiting the sodium-dependent glucose co-transporter SGLT2.

A crystalline complex between one or more natural amino acids (e.g. proline, preferably L-proline) and an SGLT2 inhibitor, is a preferred pharmaceutically acceptable form of a SGLT2 inhibitor for use according to the present invention. In particular, a crystalline complex between one or more natural amino acids (e.g. proline, preferably L-proline) and a glucopyranosyl-substituted benzene derivative SGLT2 inhibitor, preferably a SGLT2 inhibitor of formula (1), more preferably of formula (18) or yet more preferably of formula (2) (compound A) is a preferred pharmaceutically acceptable form of a SGLT2 inhibitor for use according to the present invention. A crystalline complex between one or more natural amino acids (e.g. proline, preferably L-proline) and 1-cyano-2-(4-cyclopropyl-benzyl)-4-(β-D-glucopyranos-1-yl)-benzene (compound A) is particularly preferred as a pharmaceutically acceptable form of a SGLT2 inhibitor for use according to the present invention.

Also disclosed herein is a method for making one or more crystalline complexes as defined hereinbefore and hereinafter, said method comprising the following steps:
a. preparing a solution of the SGLT2 inhibitor (e.g. a glucopyranosyl-substituted benzene derivative, or a SGLT2 inhibitor of formula (1), preferably formula (18) or more preferably formula (2), i.e. compound A) and the one or more natural amino acids in a solvent or a mixture of solvents;
b. storing the solution to precipitate the crystalline complex out of solution;
c. removing the precipitate from the solution; and
d. drying the precipitate optionally until any excess of said solvent or mixture of solvents has been removed.

A certain pharmaceutical activity is the basic prerequisite to be fulfilled by a pharmaceutically active agent before same is approved as a medicament on the market. However, there are a variety of additional requirements a pharmaceutically active agent has to comply with. These requirements are based on various parameters which are connected with the nature of the active substance itself. Without being restrictive, examples of these parameters are the stability of the active agent under various environmental conditions, its stability during production of the pharmaceutical formulation and the stability of the active agent in the final medicament compositions. The pharmaceutically active substance used for preparing the pharmaceutical compositions should be as pure as possible and its stability in long-term storage must be guaranteed under various environmental conditions. This is essential to prevent the use of pharmaceutical compositions which contain, in addition to the actual active substance, breakdown products thereof, for example. In such cases the content of active substance in the medicament might be less than that specified.

Uniform distribution of the medicament in the formulation is a critical factor, particularly when the medicament has to be given in low doses. To ensure uniform distribution, the particle size of the active substance can be reduced to a suitable level, e.g. by grinding. Since breakdown of the pharmaceutically active substance as a side effect of the grinding (or micronizing) has to be avoided as far as possible, in spite of the hard conditions required during the process, it is essential that the active substance should be highly stable throughout the grinding process. Only if the active substance is sufficiently stable during the grinding process it is possible to produce a homogeneous pharmaceutical formulation which always contains the specified amount of active substance in a reproducible manner.

Another problem which may arise in the grinding process for preparing the desired pharmaceutical formulation is the input of energy caused by this process and the stress on the surface of the crystals. This may in certain circumstances lead to polymorphous changes, to amorphization or to a change in the crystal lattice. Since the pharmaceutical quality of a pharmaceutical formulation requires that the active substance should always have the same crystalline morphology, the stability and properties of the crystalline active substance are subject to stringent requirements from this point of view as well.

The stability of a pharmaceutically active substance is also important in pharmaceutical compositions for determining the shelf life of the particular medicament; the shelf life is the length of time during which the medicament can be administered without any risk. High stability of a medicament in the abovementioned pharmaceutical compositions under various storage conditions is therefore an additional advantage for both the patient and the manufacturer.

The absorption of moisture reduces the content of pharmaceutically active substance as a result of the increased weight caused by the uptake of water. Pharmaceutical compositions with a tendency to absorb moisture have to be protected from moisture during storage, e.g. by the addition of suitable drying agents or by storing the drug in an environment where it is protected from moisture. Preferably, therefore, a pharmaceutically active substance should be at best slightly hygroscopic.

Furthermore, the availability of a well-defined crystalline form allows the purification of the drug substance by recrystallization.

Apart from the requirements indicated above, it should be generally borne in mind that any change to the solid state of a pharmaceutical composition which is capable of improving its physical and chemical stability gives a significant advantage over less stable forms of the same medicament.

A crystalline complex between a natural amino acid and an SGLT2 inhibitor (e.g. a glucopyranosyl-substituted benzene derivative or a SGLT2 inhibitor of formula (1), or formula (18) or, particularly, of formula (2), i.e. compound A) fulfills important requirements mentioned hereinbefore.

Preferably the natural amino acid is present in either its (D) or (L) enantiomeric form, most preferably as the (L) enantiomer.

Furthermore those crystalline complexes according to this invention are preferred which are formed between the SGLT2 inhibitor (e.g. of formula (1), preferably formula (18) or, particularly, of formula (2), i.e. compound A) and one natural amino acid, most preferably between the compound A and the (L) enantiomer of a natural amino acid.

Preferred amino acids according to this invention are selected from the group consisting of phenylalanine and proline, in particular (L)-proline and (L)-phenylalanine.

According to a preferred embodiment the crystalline complex is characterized in that the natural amino acid is proline, in particular (L)-proline.

Preferably the molar ratio of the SGLT2 inhibitor (e.g. of formula (1), preferably formula (18) or, particularly, of formula (2), i.e. compound A) and the natural amino acid is in the range from about 2:1 to about 1:3; more preferably from about 1.5:1 to about 1:1.5, even more preferably from about 1.2:1 to about 1:1.2, most preferably about 1:1. In the following such an embodiment is referred to as "complex (1:1)" or "1:1 complex".

Therefore a preferred crystalline complex according to this invention is a complex (1:1) between said SGLT2 inhibitor (e.g. of formula (1), preferably formula (18) or, particularly, of formula (2), i.e. compound A) and proline; in particular of said SGLT2 inhibitor and L-proline.

According to a preferred embodiment the crystalline complex, in the particular the 1:1 complex of said SGLT2 inhibitor with L-proline, is a hydrate.

Preferably the molar ratio of the crystalline complex and water is in the range from about 1:0 to 1:3; more preferably from about 1:0 to 1:2, even more preferably from about 1:0.5 to 1:1.5, most preferably about 1:0.8 to 1:1.2, in particular about 1:1.

The crystalline complex of said SGLT2 inhibitor with proline, in particular with L-proline and water, may be identified and distinguished from other crystalline forms by means of their characteristic X-ray powder diffraction (XRPD) patterns.

For example, a crystalline complex of compound A with L-proline is preferably characterized by an X-ray powder diffraction pattern that comprises peaks at 20.28, 21.14 and 21.64 degrees 2Θ (±0.1 degrees 2Θ), wherein said X-ray powder diffraction pattern is made using CuK$_{\alpha 1}$ radiation.

In particular said X-ray powder diffraction pattern comprises peaks at 4.99, 20.28, 21.14, 21.64 and 23.23 degrees 2Θ (±0.1 degrees 2Θ), wherein said X-ray powder diffraction pattern is made using CuK$_{\alpha 1}$ radiation.

More specifically said X-ray powder diffraction pattern comprises peaks at 4.99, 17.61, 17.77, 20.28, 21.14, 21.64, 23.23 and 27.66 degrees 2Θ (±0.1 degrees 2Θ), wherein said X-ray powder diffraction pattern is made using CuK$_{\alpha 1}$ radiation.

Even more specifically said X-ray powder diffraction pattern comprises peaks at 4.99, 15.12, 17.61, 17.77, 18.17, 20.28, 21.14, 21.64, 23.23 and 27.66 degrees 2Θ (±0.1 degrees 2Θ), wherein said X-ray powder diffraction pattern is made using CuK$_{\alpha 1}$ radiation.

Even more specifically, the crystalline complex of compound A and L-proline is characterized by an X-ray powder diffraction pattern, made using CuK$_{\alpha 1}$ radiation, which comprises peaks at degrees 2Θ (±0.1 degrees 2Θ) as contained in Table 1.

TABLE 1

X-ray powder diffraction pattern of the crystalline complex of compound A and L-proline (only peaks up to 30° in 2 Θ are listed):

| 2 Θ [°] | d-value [Å] | Intensity I/I$_0$ [%] |
| --- | --- | --- |
| 4.99 | 17.68 | 39 |
| 7.01 | 12.61 | 6 |
| 8.25 | 10.70 | 11 |
| 9.95 | 8.88 | 12 |
| 13.15 | 6.73 | 30 |
| 13.33 | 6.64 | 10 |
| 14.08 | 6.28 | 4 |
| 15.12 | 5.85 | 32 |
| 16.40 | 5.40 | 12 |
| 16.49 | 5.37 | 13 |
| 17.11 | 5.18 | 6 |
| 17.61 | 5.03 | 32 |
| 17.77 | 4.99 | 35 |
| 18.17 | 4.88 | 32 |
| 18.32 | 4.84 | 28 |
| 18.72 | 4.74 | 8 |
| 19.16 | 4.63 | 30 |
| 19.96 | 4.45 | 26 |
| 20.28 | 4.37 | 56 |
| 20.60 | 4.31 | 7 |
| 21.14 | 4.20 | 84 |
| 21.64 | 4.10 | 100 |
| 22.33 | 3.98 | 15 |
| 23.23 | 3.83 | 41 |
| 24.06 | 3.70 | 4 |
| 24.51 | 3.63 | 15 |
| 24.93 | 3.57 | 26 |
| 25.89 | 3.44 | 23 |
| 26.21 | 3.40 | 11 |
| 26.84 | 3.32 | 8 |
| 27.66 | 3.22 | 38 |
| 27.96 | 3.19 | 9 |
| 28.26 | 3.16 | 5 |
| 28.44 | 3.14 | 6 |
| 28.75 | 3.10 | 6 |
| 29.18 | 3.06 | 19 |

Even more specifically, said crystalline complex is characterized by an X-ray powder diffraction pattern, made using CuK$_{\alpha 1}$ radiation, which comprises peaks at degrees 2Θ (±0.1 degrees 2Θ as shown in FIG. 11).

Furthermore said crystalline complex of the compound A with L-proline is characterized by a melting point of above 89° C., in particular in a range from about 89° C. to about 115° C., more preferably in a range from about 89° C. to about 110° C. (determined via DSC; evaluated as onset-temperature; heating rate 10 K/min). It can be observed that this crystalline complex melts under dehydration. The obtained DSC curve is shown in FIG. 12.

Said crystalline complex of the compound A with L-proline shows a weight loss by thermal gravimetry (TG). The observed weight loss indicates that the crystalline form contains water which may be bound by adsorption and/or may be part of the crystalline lattice, i.e. the crystalline form may be present as a crystalline hydrate. The content of water in the crystalline form lies in the range from 0 to about 10 weight-%, in particular 0 to about 5 weight-%, even more preferably from about 1.5 to about 5 weight-%. The dotted line in FIG. 2 depicts a weight loss of between 2.8 and 3.8% of water. From the observed weight loss a stoichiometry close to a monohydrate can be estimated.

Said crystalline complex has advantageous physico-chemical properties which are beneficial in the preparation of a pharmaceutical composition. In particular the crystalline complex has a high physical and chemical stability under various environmental conditions and during the production of a medicament. For example the crystals can be obtained in a shape and particle size which are particular suitable in a production method for solid pharmaceutical formulations. In addition the crystals show a high mechanical stability that allows grinding of the crystals. Furthermore the crystalline complex does not show a high tendency to absorb moisture and is chemically stable, i.e. the crystalline complex allows the production of a solid pharmaceutical formulation with a long shelf life. On the other hand the crystalline complex has a favorably high solubility over a wide pH-range which is advantageous in solid pharmaceutical formulations for oral administration.

The X-ray powder diffraction patterns may be recorded using a STOE-STADI P-diffractometer in transmission mode fitted with a location-sensitive detector (OED) and a Cu-anode as X-ray source (CuK$_{\alpha 1}$ radiation, λ=1.54056 Å, 40 kV, 40 mA). In Table 1 the values "2Θ [°]" denote the angle of diffraction in degrees and the values "d [Å]" denote the specified distances in Å between the lattice planes. The intensity shown in FIG. 11 is given in units of cps (counts per second).

In order to allow for experimental error, the above described 2 Θ values should be considered accurate to ±0.1 degrees 2 Θ, in particular ±0.05 degrees 2 Θ. That is to say, when assessing whether a given sample of crystals of the compound A is the crystalline form in accordance with the above described 2 Θ values, a 2 Θ value which is experimentally observed for the sample should be considered identical with a characteristic value described above if it falls within ±0.1 degrees 2 Θ of the characteristic value, in particular if it falls within ±0.05 degrees 2 Θ of the characteristic value.

The melting point is determined by DSC (Differential Scanning calorimetry) using a DSC 821 (Mettler Toledo). The weight loss is determined by thermal gravimetry (TG) using a TGA 851 (Mettler Toledo).

Also disclosed herein is a method for making a crystalline complex as defined hereinbefore and hereinafter, said method comprising the following steps:
 a. preparing a solution of an SGLT2 inhibitor as described herein (e.g. compound A or another SGLT2 inhibitor described herein) and the one or more natural amino acids in a solvent or a mixture of solvents;
 b. storing the solution to precipitate the crystalline complex out of solution;
 c. removing the precipitate from the solution; and
 d. drying the precipitate optionally until any excess of said solvent or mixture of solvents has been removed.

According to step (a) a solution of the SGLT2 inhibitor (e.g. compound A or another SGLT2 inhibitor described herein) and the one or more natural amino acids in a solvent or a mixture of solvents is prepared. Preferably the solution is saturated or at least nearly saturated or even supersaturated with respect to the crystalline complex. In the step (a) the SGLT2 inhibitor may be dissolved in a solution comprising the one or more natural amino acids or the one or more natural amino acids may be dissolved in a solution comprising the SGLT2 inhibitor. According to an alternative procedure the SGLT2 inhibitor is dissolved in a solvent or mixture of solvents to yield a first solution and the one or more natural amino acids are dissolved in a solvent or mixture of solvents to yield a second solution. Thereafter said first solution and said second solution are combined to form the solution according to step (a).

Preferably the molar ratio of the natural amino acid and the SGLT2 inhibitor (e.g. compound A or any other SGLT2 inhibitor described herein) in the solution corresponds to the molar ratio of the natural amino acid and the SGLT2 inhibitor in the crystalline complex to be obtained. Therefore a preferred molar ratio is in the range from about 1:2 to 3:1; most preferably about 1:1.

Suitable solvents are preferably selected from the group consisting of C$_{1-4}$-alkanols, water, ethyl acetate, acetonitrile, acetone, diethyl ether, tetrahydrofuran, and mixture of two or more of these solvents.

More preferred solvents are selected from the group consisting of methanol, ethanol, isopropanol, water and mixture of two or more of these solvents, in particular mixtures of one or more of said organic solvents with water.

Particularly preferred solvents are selected from the group consisting of ethanol, isopropanol, water and mixtures of ethanol and/or isopropanol with water.

In case a mixture of water and one or more C$_{1-4}$-alkanols, in particular of methanol, ethanol and/or isopropanol, most preferably of ethanol, is taken, a preferred volume ratio of water:the alkanol is in the range from about 99:1 to 1:99; more preferably from about 50:1 to 1:80; even more preferably from about 10:1 to 1:60.

Preferably the step (a) is carried out at about room temperature (about 20° C.) or at an elevated temperature up to about the boiling point of the solvent or mixture of solvents used.

According to a preferred embodiment the starting material of the SGLT2 inhibitor (e.g. compound A or any other SGLT2 inhibitor described herein) and/or of the one or more natural amino acids and/or of the solvent and mixtures of solvents contain an amount of H$_2$O which is at least the quantity required to form a hydrate of the SGLT2 inhibitor; in particular at least 1 mol, preferably at least 1.5 mol of water per mol of SGLT2 inhibitor. Even more preferably the amount of water is at least 2 mol of water per mol of SGLT2 inhibitor. This means that either the SGLT2 inhibitor (e.g. compound A) as starting material or the one or more natural amino acids or said solvent or mixture of solvents, or said compounds and/or solvents in combination contain an amount of H$_2$O as specified above. For example if the starting material of the SGLT2 inhibitor (e.g. compound A) or of the natural amino acid in step (a) does contain sufficient water as specified above, a water content of the solvent(s) is not mandatory.

In order to reduce the solubility of the crystalline complex according to this invention in the solution, in step (a) and/or in step (b) one or more antisolvents may be added, preferably during step (a) or at the beginning of step (b). Water is an example of a suitable antisolvent. The amount of antisolvent is preferably chosen to obtain a supersaturated or saturated solution with respect to the crystalline complex.

In step (b) the solution is stored for a time sufficient to obtain a precipitate, i.e. the crystalline complex. The temperature of the solution in step (b) is about the same as or lower than in step (a). During storage the temperature of the solution is preferably lowered, preferably to a temperature in the range of 20° C. to 0° C. or even lower. The step (b) can be carried out with or without stirring. As known to the one skilled in the art by the period of time and the difference of temperature in step (b) the size, shape and quality of the obtained crystals can be controlled. Furthermore the crystallization may be induced by methods as known in the art, for example by mechanical means such as scratching or rubbing the contact surface of the reaction vessel for example with a glass rod. Optionally the (nearly) saturated or supersaturated solution may be inoculated with seed crystals.

In step (c) the solvent(s) can be removed from the precipitate by known methods as for example filtration, suction filtration, decantation or centrifugation.

In step (d) an excess of the solvent(s) is removed from the precipitate by methods known to the one skilled in the art as for example by reducing the partial pressure of the solvent(s), preferably in vacuum, and/or by heating above ca. 20° C., preferably in a temperature range below 100° C., even more preferably below 85° C.

Compound A may be synthesized by methods as specifically and/or generally described or cited in international application WO 2007/128749 which in its entirety is incorporated herein by reference, and/or in the Examples disclosed herein below. Biological properties of the compound A may also be investigated as is described in WO 2007/128749.

A crystalline complex as described herein is preferably employed as drug active substance in substantially pure form, that is to say, essentially free of other crystalline forms of the SGLT2 inhibitor (e.g. compound A). Nevertheless, the invention also embraces a crystalline complex in admixture with another crystalline form or forms. Should the drug active substance be a mixture of crystalline forms, it is preferred that the substance comprises at least 50%-weight, even more preferably at least 90%-weight, most preferably at least 95%-weight of the crystalline complex as described herein.

In view of its ability to inhibit SGLT activity, a crystalline complex according to the invention is suitable for the use in the treatment and/or preventive treatment of conditions or diseases which may be affected by the inhibition of SGLT activity, particularly SGLT-2 activity, in particular the metabolic disorders as described herein. The crystalline complex according to the invention is also suitable for the preparation of pharmaceutical compositions for the treatment and/or preventive treatment of conditions or diseases which may be affected by the inhibition of SGLT activity, particularly SGLT-2 activity, in particular metabolic disorders as described herein. A crystalline complex as described herein (in particular of compound A with a natural amino acid, e.g. proline, particularly L-proline) is also suitable for the use in the treatment of felines.

Pharmaceutical Compositions and Formulations

SGLT2 inhibitors for use according to the invention may be prepared as pharmaceutical compositions. They may be prepared as solid or as liquid formulations. In either case, they are preferably prepared for oral administration, preferably in liquid form for oral administration. The SGLT2 inhibitors may, however, also be prepared, e.g., for parenteral administration.

Solid formulations include tablets, granular forms, and other solid forms such as suppositories. Among solid formulations, tablets and granular forms are preferred.

Pharmaceutical compositions within the meaning of the present invention may comprise an SGLT2 inhibitor according to the present invention and one or more excipients. Any excipient that allows for, or supports, the intended medical effect may be used. Such excipients are available to the skilled person. Useful excipients are for example antiadherents (used to reduce the adhesion between the powder (granules) and the punch faces and thus prevent sticking to tablet punches), binders (solution binders or dry binders that hold the ingredients together), coatings (to protect tablet ingredients from deterioration by moisture in the air and make large or unpleasant-tasting tablets easier to swallow), disintegrants (to allow the tablet to break upon dilution), fillers, diluents, flavors, colors, glidants (flow regulators—to promote powder flow by reducing interparticle friction and cohesion), lubricants (to prevent ingredients from clumping together and from sticking to the tablet punches or capsule filling machine), preservatives, sorbents, sweeteners etc.

Formulations according to the invention, e.g. solid formulations, may comprise carriers and/or disintegrants selected from the group of sugars and sugar alcohols, e.g. mannitol, lactose, starch, cellulose, microcrystalline cellulose and cellulose derivatives, e.g. methylcellulose, and the like.

Manufacturing procedures for formulations suitable for feline animals are known to the person skilled in the art, and for solid formulations comprise, e.g., direct compression, dry granulation and wet granulation. In the direct compression process, the active ingredient and all other excipients are placed together in a compression apparatus that is directly applied to press tablets out of this material. The resulting tablets can optionally be coated afterwards in order to protect them physically and/or chemically, e.g. by a material known from the state of the art.

A unit for administration, e.g. a single liquid dose or a unit of a solid formulation, e.g. a tablet, may comprise 0.1 mg to 10 mg, or e.g. 0.3 mg to 1 mg, 1 mg to 3 mg, 3 mg to 10 mg; or 5 to 2500 mg, or e.g. 5 to 2000 mg, 5 mg to 1500 mg, 10 mg to 1500 mg, 10 mg to 1000 mg, or 10-500 mg of an SGLT2 inhibitor for use according to the invention. As the skilled person would understand, the content of the SGLT2 inhibitor in a solid formulation, or any formulation as disclosed herein for administration to a feline animal, may be increased or decreased as appropriate in proportion to the body weight of the feline animal to be treated.

In one embodiment a pharmaceutical composition for use according to the invention is designed for oral or parenteral administration, preferably for oral administration. Especially the oral administration is ameliorated by excipients which modify the smell and/or haptic properties of the pharmaceutical composition for the intended patient, e.g. as described.

When the SGLT2 inhibitor for use according to the invention is formulated for oral administration, it is preferred that excipients confer properties, e.g. palatability and/or chewability that render the formulation suitable for administration to a feline animal.

Also preferred are liquid formulations. Liquid formulations may be, e.g., solutions, syrups or suspensions. They may be administered directly to the feline animal or may be mixed with the food and/or drink (e.g. drinking water, or the like) of the feline animal. One advantage of a liquid formulation (similar to a formulation in granular form), is that such a dosage form allows precise dosing. For example, the SGLT2 inhibitor may be dosed precisely in proportion to the body mass of a feline animal. Typical compositions of liquid formulations are known to the person skilled in the art.

Dosing and Administration

A practitioner skilled in the art can determine suitable doses for the uses of the present invention. Preferred units dosing units include mg/kg, i.e. mg SGLT2 inhibitor per body mass of the feline animal. An SGLT2 inhibitor of the invention may, e.g., be administered in doses of 0.01-5 mg/kg per day, e.g. 0.01-4 mg/kg, e.g. 0.01-3 mg/kg, e.g. 0.01-2 mg/kg, e.g. 0.01-1.5 mg/kg, e.g., 0.01-1 mg/kg, e.g. 0.01-0.75 mg/kg, e.g. 0.01-0.5 mg/kg, e.g. 0.01-0.4 mg/kg, e.g. 0.01-0.4 mg/kg per day; or 0.1 to 3.0 mg/kg per day, preferably from 0.2 to 2.0 mg/kg per day, more preferably from 0.1 to 1 mg/kg per day. In another preferred embodiment the dose is 0.02-0.5 mg/kg per day, more preferably 0.03-0.4 mg/kg per day, e.g. 0.03-0.3 mg/kg per day.

A practitioner skilled in the art is able to prepare an SGLT2 inhibitor of the invention for administration according to a desired dose.

Preferably, according to the invention, an SGLT2 inhibitor is administered no more than three times per day, more preferably no more than twice per day, most preferably only once per day. The frequency of administration can be adapted to the typical feeding rate of the feline animal.

According to the invention, an SGLT2 inhibitor may be administered such that an appropriate blood plasma concentration of the SGLT2 inhibitors is achieved (e.g. a maximal blood plasma concentration, or blood plasma concentration after a given time, e.g. 4, 8, 12 or 24 hours after oral administration, preferably about 8 hours after oral administration). E.g., for compound A, the blood plasma concentration (e.g. maximal blood plasma concentration or blood plasma concentration after said given time after oral administration) may be within the range 2 to 4000 nM, e.g. 20 to 3000, or e.g. 40 to 2000 nM.

Preferably, following administration and the time required for an SGLT2 inhibitor to reach the bloodstream, such levels are maintained in the blood over a time interval of at least 12 hours, more preferably at least 18 hours, most preferably at least 24 h.

Preferably, according to the invention, an SGLT2 inhibitor is administered orally, in liquid or solid form. The SGLT2 inhibitor may be administered directly to the animals mouth (e.g. using a syringe, preferably a body-weight-graduated syringe) or together with the animal's food or drink (e.g. with its drinking water or the like), in each case preferably in liquid form. The SGLT2 inhibitor may, however, also be administered, e.g., parenterally, or by any other route of administration, e.g., rectally.

The SGLT2 inhibitor may be used alone or in combination with another drug. In some embodiments, one or more SGLT2 inhibitors, preferably compound A, is used in combination with one or more further oral antihyperglycemic drugs. When the SGLT2 inhibitor is used in combination with a further drug, the SGLT2 inhibitor and any further drug may be administered simultaneously, sequentially (in any order), and/or according to a chronologically staggered dosage regime. In such embodiments, when a further drug for combined administration with an SGLT2 inhibitor or is not administered simultaneously with an SGLT2 inhibitor, the SGLT2 inhibitor and any further drug are preferably administered within a period of at least 2 weeks, 1 month, 2 months, 4 months, 6 months or longer, e.g. 12 months or more.

In some embodiments the SGLT2 inhibitor (whether used alone or in combination with another drug) is not used in combination with 1-[(3-cyano-pyridin-2-yl)methyl]-3-methyl-7-(2-butyn-1-yl)-8-[3-(R)-amino-piperidin-1-yl]-xanthine or a pharmaceutically acceptable salt thereof, i.e. the feline animal is not treated with said compound. In some embodiments the SGLT2 inhibitor is not used in combination with a DPP-IV inhibitor, i.e., the feline animal is not treated with a DPP-IV inhibitor.

In some embodiments, the SGLT2 inhibitor is used as a monotherapy, i.e. stand-alone therapy, i.e. no other medication is administered to the feline animal for the treatment or prevention of the same metabolic disorder, i.e. the metabolic disorder for which the SGLT2 inhibitor is administered. E.g., no other medication is administered to the feline animal for the treatment or prevention of the same metabolic disorder within a period of at least 2, 3, or 4 weeks before and after administration of the SGLT2 inhibitor.

EXAMPLES

Figure 1:
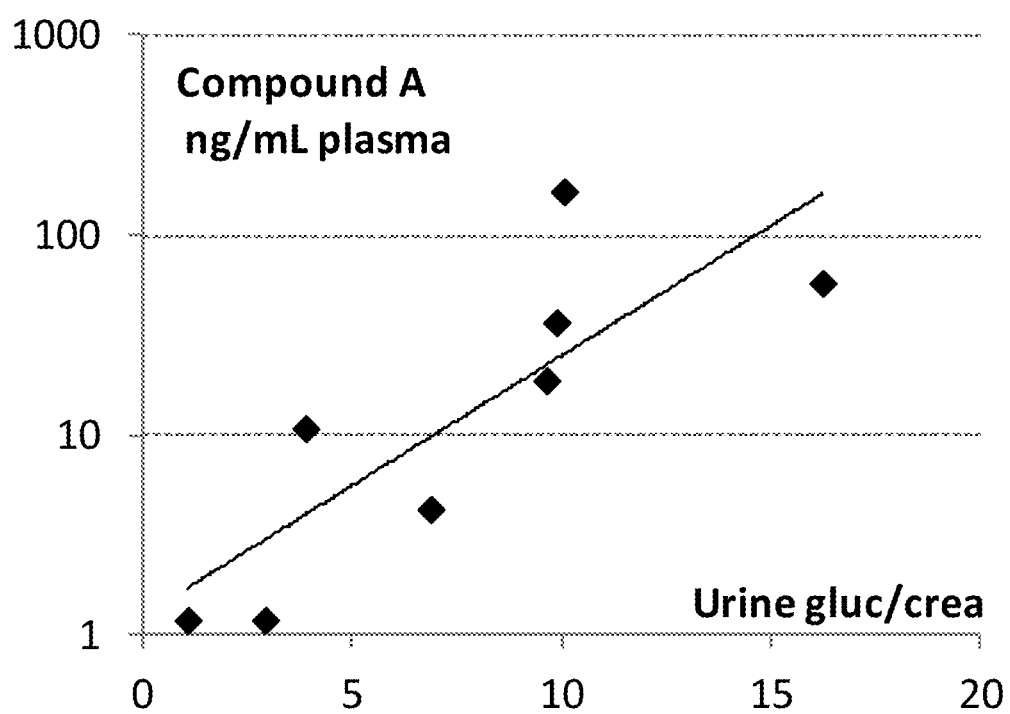
FIG. 1 shows the correlation between compound A plasma level and urinary glucose excretion normalized to creatinine (gluc/crea). There is a clear logarithmic-linear relationship.
Figure 2A:
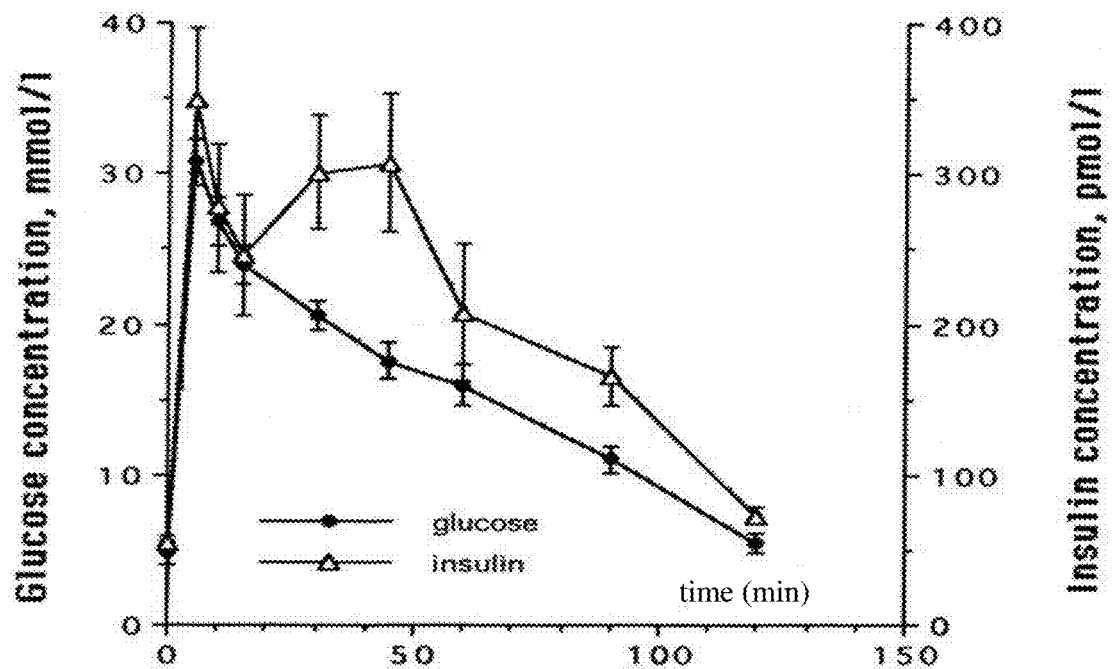
FIG. 2A shows the blood glucose and insulin secretion profiles in an intravenous glucose tolerance test (ivGTT) of normal lean cats according to Hoenig (Mol Cell Endocrinal 2002, 197(1-2): 221-229) (iv GTT [1 g/kg]) and of insulin resistant obese cats before (dotted line-pretests, "pre") and after 4 weeks of treatment with compound A (solid line) (FIG. 2B). The increased and prolonged second phase of the insulin resistant obese cats used in the present study was significantly improved by treatment with compound A.
Figure 2B:
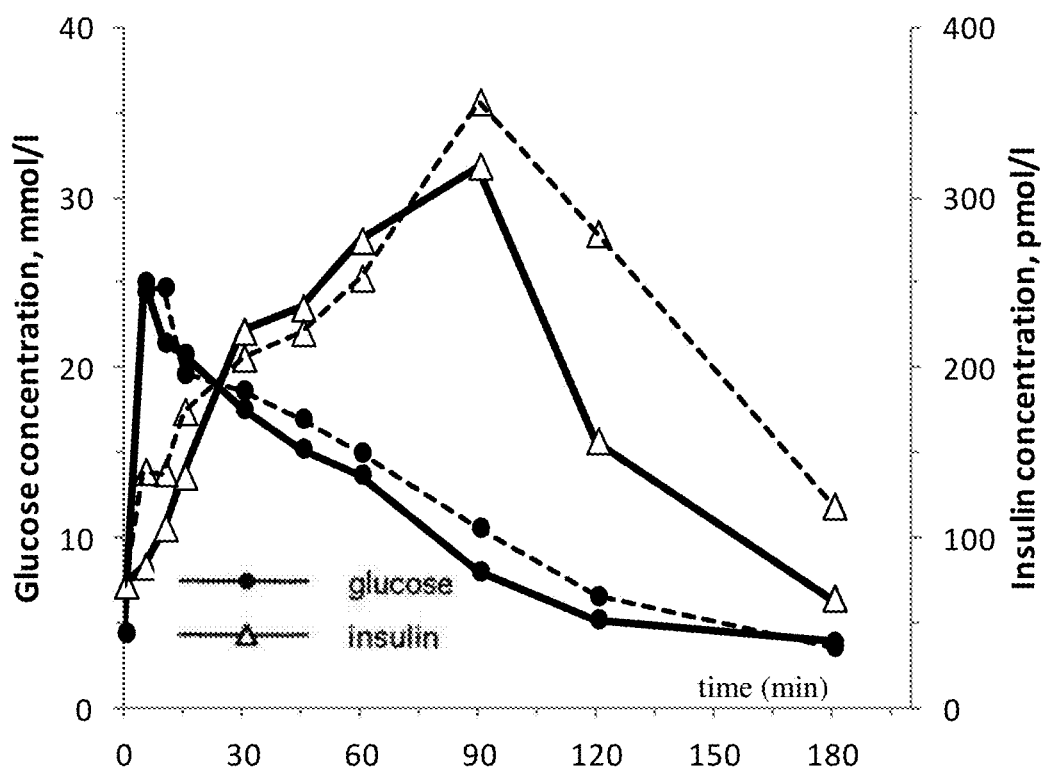
Figure 3A:
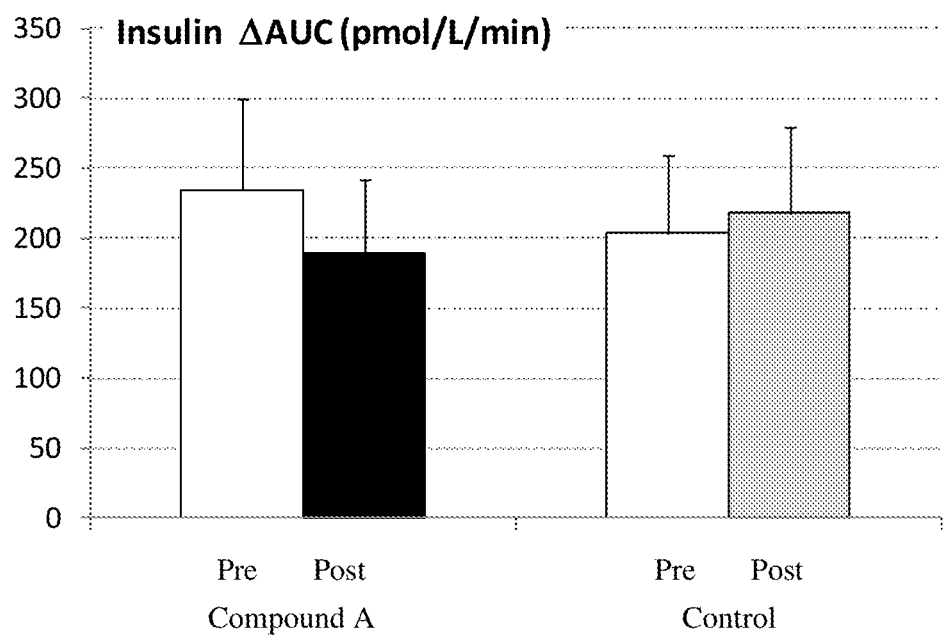
FIG. 3A shows area-under-curve (AUC) values of blood insulin and a surrogate insulin sensitivity index (blood insulin-to-glucose relationship as expressed by the modified Belfiore index) in insulin resistant cats during an intravenous glucose tolerance test (ivGTT) before ("pre") and after ("post") 4 weeks of treatment with compound A or its vehicle ("control"). Treatment with compound A leads to a significant reduction of Insulin AUC (panel A), and significantly improved insulin sensitivity FIG. 3B).
Figure 3B:
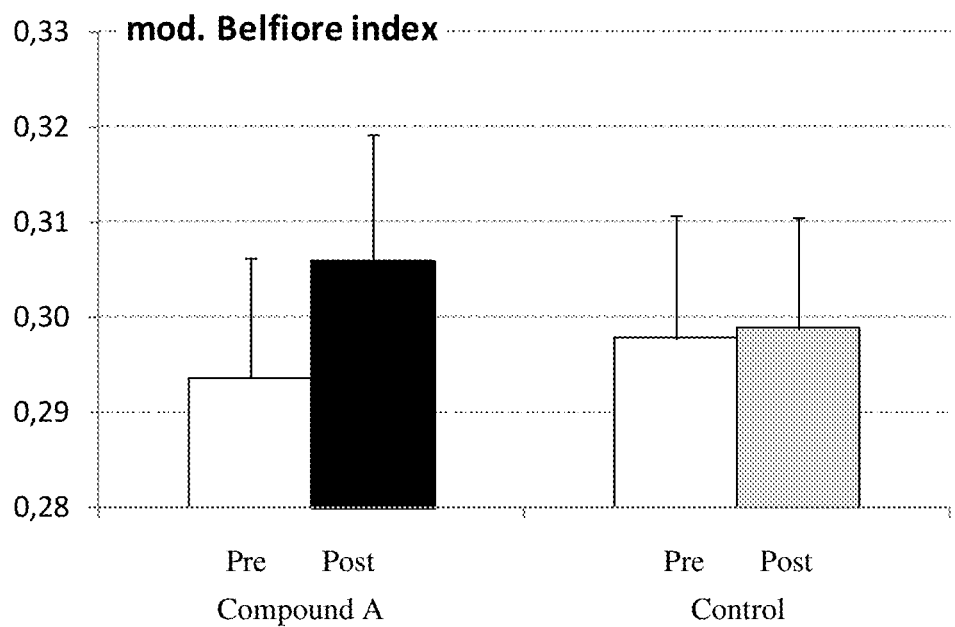
Figure 4A:
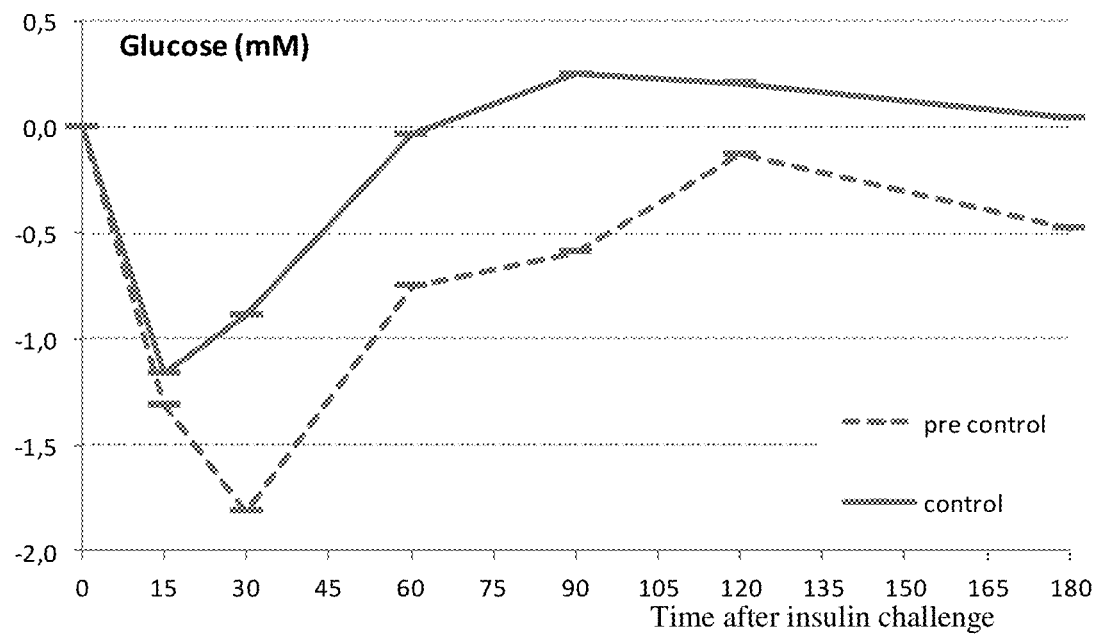
FIGS. 4A and 4B show time courses of blood glucose concentrations [mmol/L] after insulin challenge in insulin resistant cats during an intravenous insulin tolerance test (ivITT) before (dotted line pretests, "pre") and after 4 weeks of treatment (solid line) with compound A or its vehicle ("control"). In untreated animals (controls) insulin sensitivity (IS) decreased throughout the study (FIG. 4A). In comparison, treatment with compound A was associated with a significant improvement in IS (FIG. 4B).
Figure 4B:
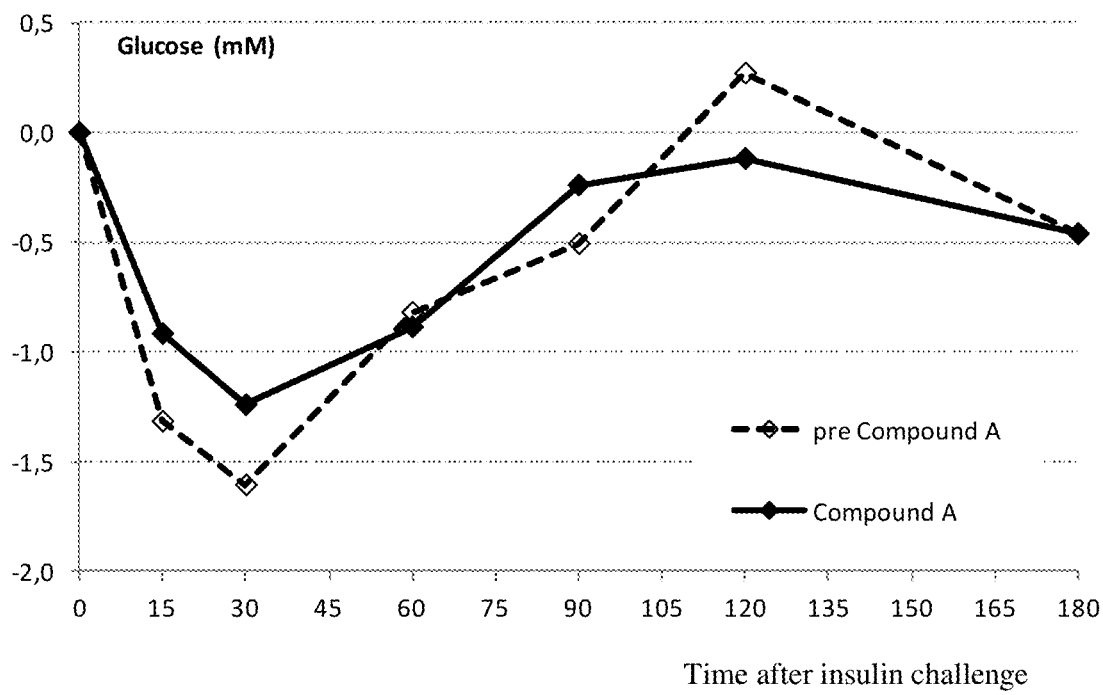
Figure 5A:
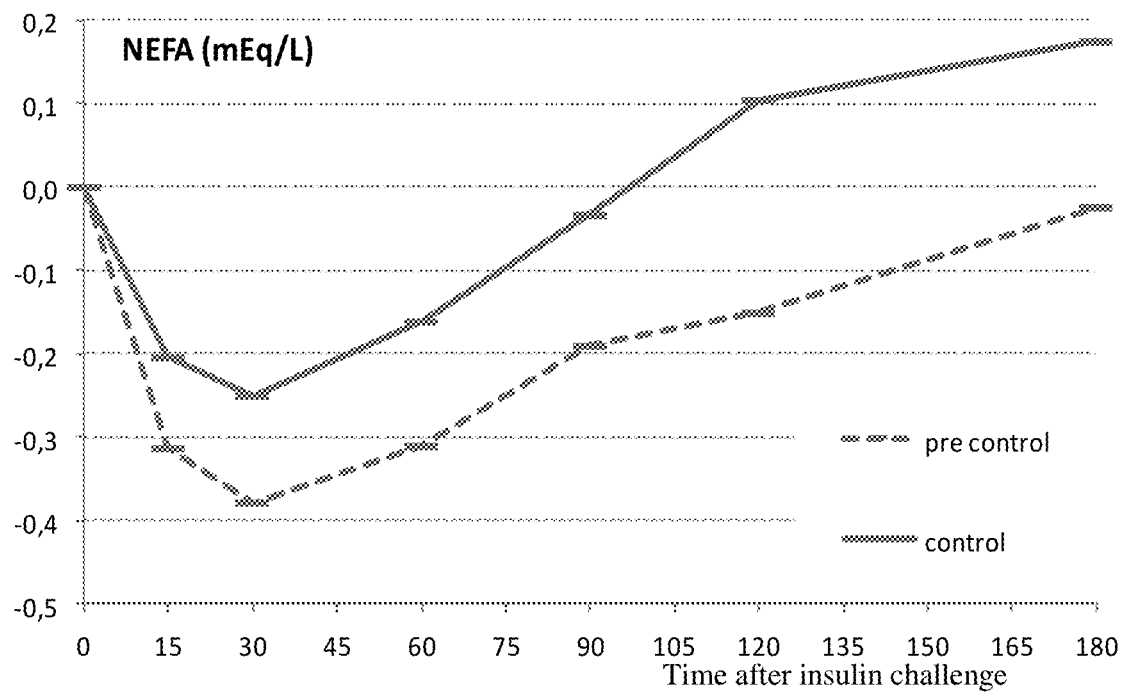
FIGS. 5A and 5B show time courses of non-esterified fatty acid (NEFA) levels in blood [mEq/L] after insulin challenge in insulin resistant cats during an ivITT before (dotted line pretests, "pre") and after 4 weeks of treatment (solid line) with compound A or its vehicle ("control"). In untreated animals (controls) NEFA elimination significantly worsened throughout the study period (FIG. 5A), whereas it was significantly improved by treatment with compound A (FIG. 5B).
Figure 5B:
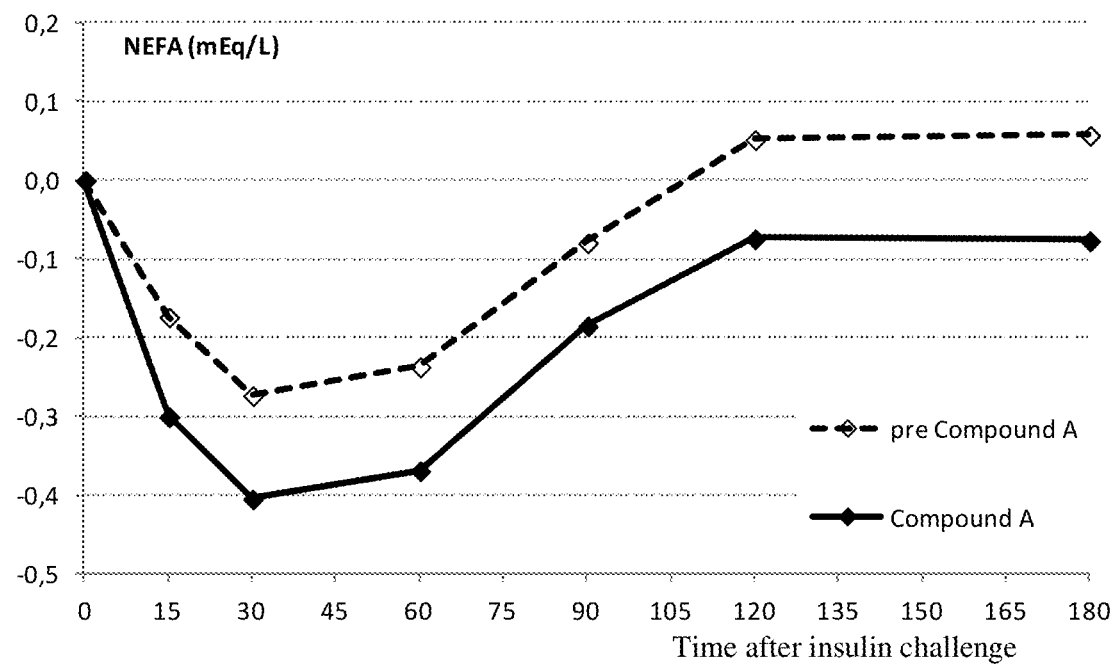
Figure 6:
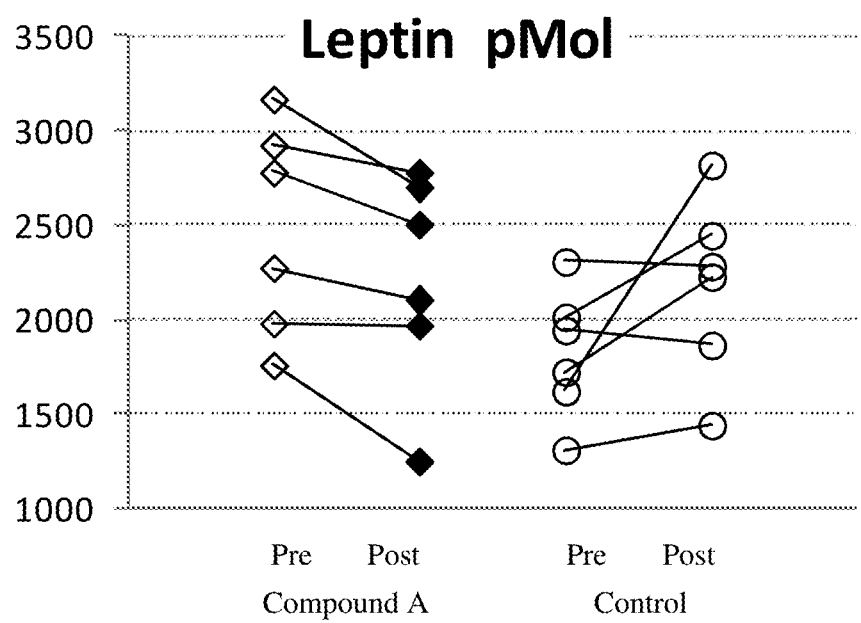
FIG. 6. shows that blood leptin concentrations significantly decreased over the study period in the treated cats.
Figure 7:
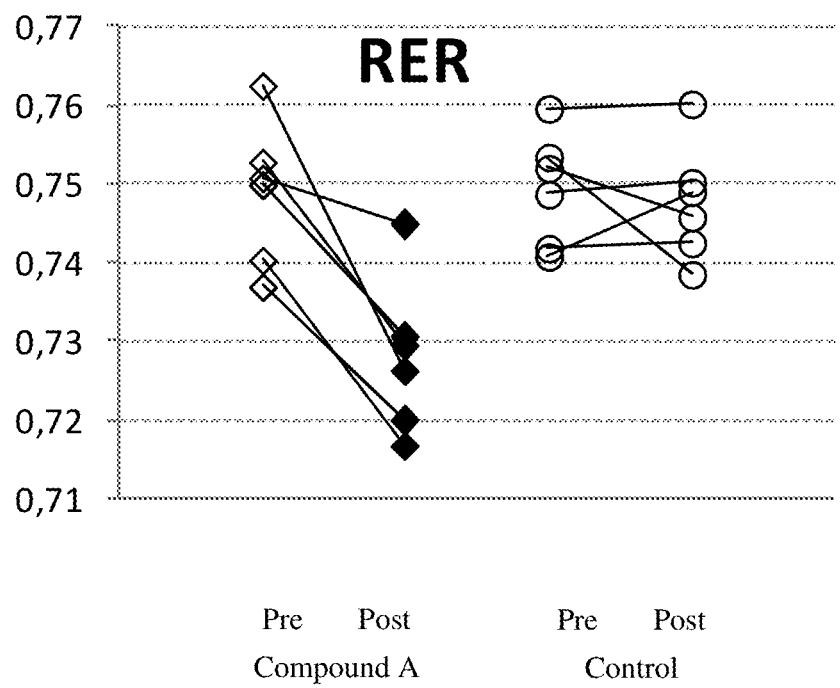
FIG. 7 shows a reduction of the respiratory exchange ratio (RER) (indicating increased lipid utilization) in treated animals, as measured by indirect calorimetry.
Figure 8:
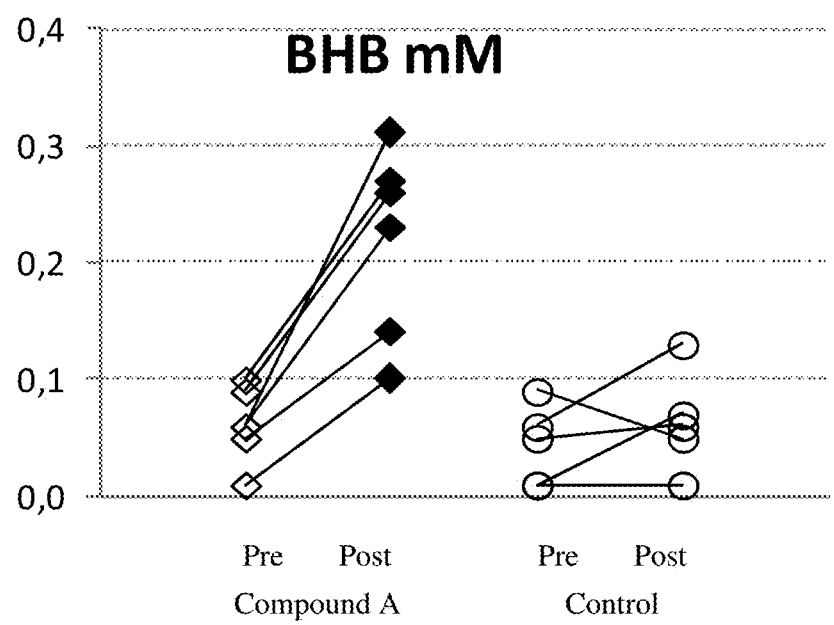
FIG. 8 shows that β-hydroxybutyrate levels in blood (β-HB/BHB) increased following 4 weeks of treatment with compound A.
Figure 9:
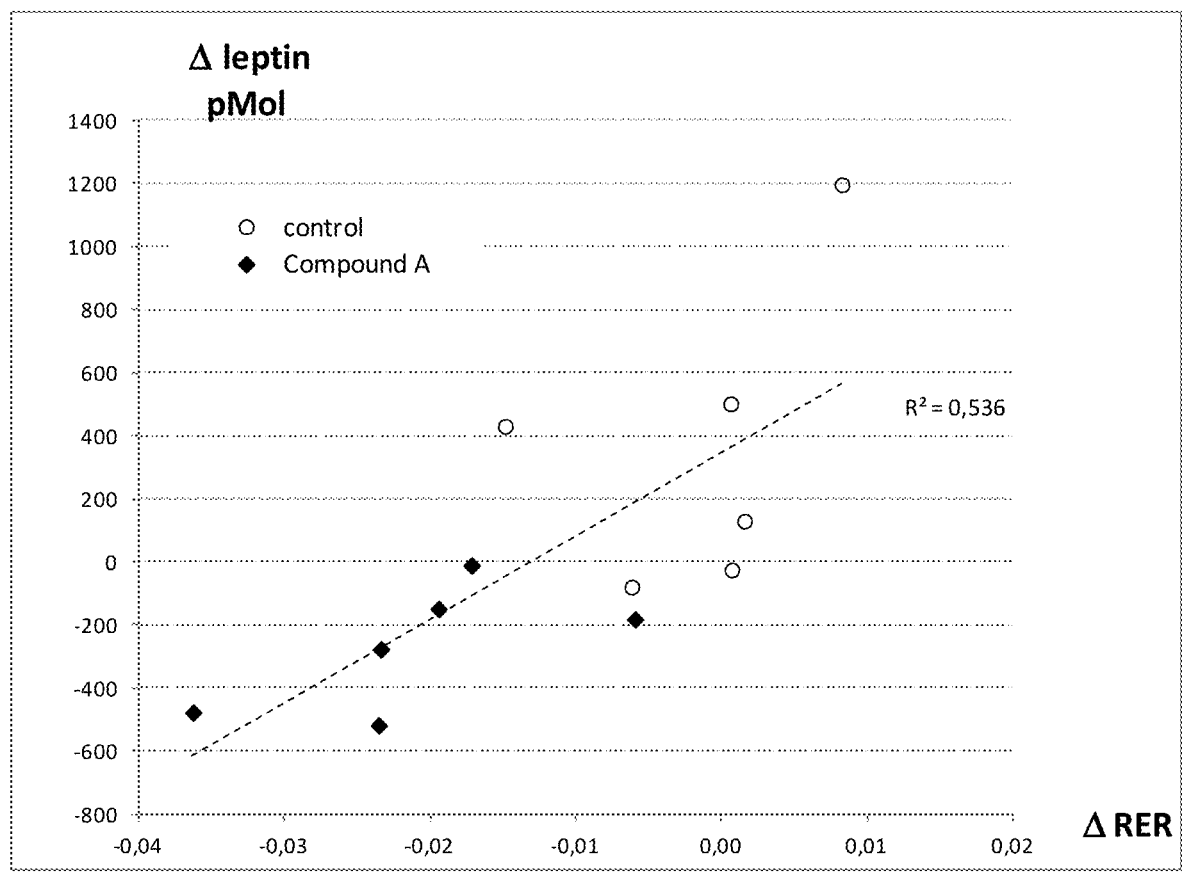
FIG. 9 shows the positive correlation between the change of blood leptin concentration and the change of RER before and after 4 weeks of treatment with compound A or vehicle (control).
Figure 10:
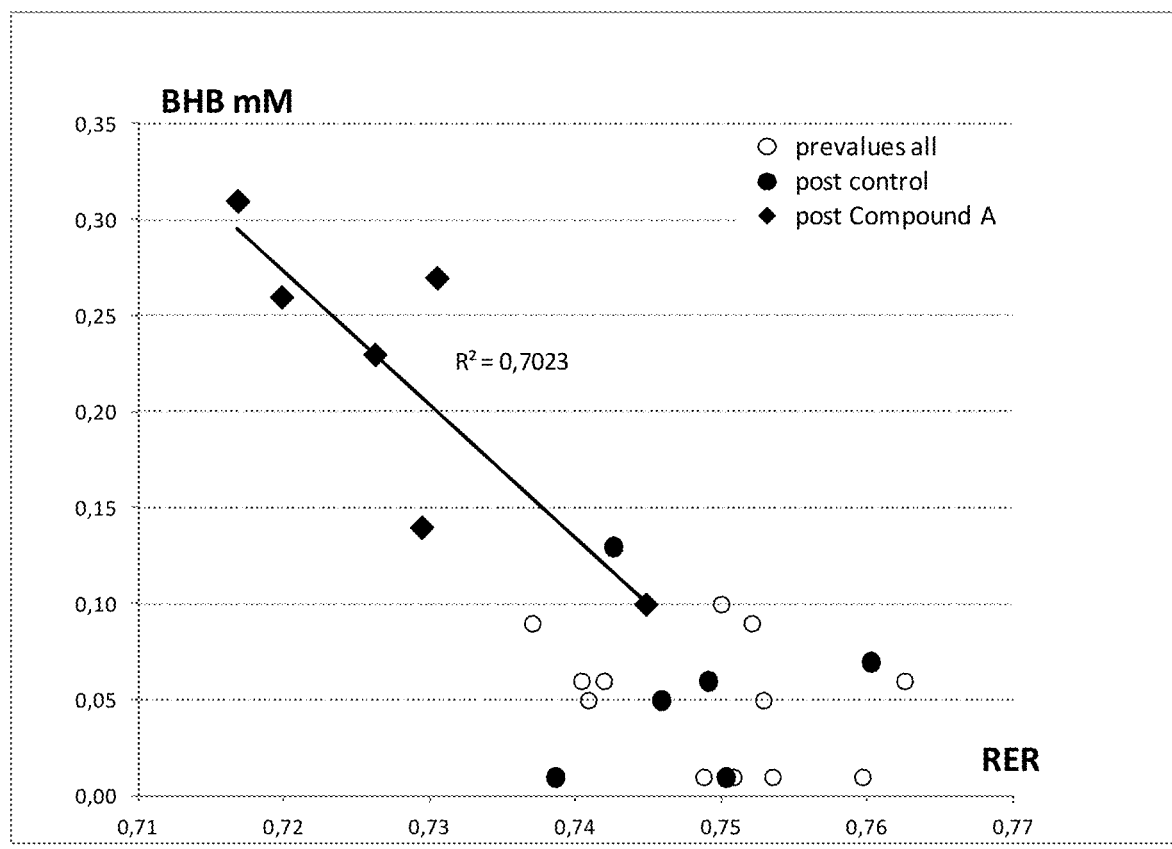
FIG. 10 shows the negative correlation between β-hydroxybutyrate levels in blood (β-HB/BHB) and the RER after 4 weeks of treatment with compound A.

The following examples show the beneficial therapeutic effects on glycemic control and/or insulin resistance, etc., of using one or more SGLT2 inhibitors in feline animals, according to the present invention. These examples are intended to illustrate the invention in more detail without any limitation of the scope of the claims.

Example 1 Pharmacokinetics (PK)/Pharmacodynamics (PD) of Compound a Single Oral Dosing in Cats Compound A was administered to overnight fasted cats. The groups (n=3 per group) received a single oral administration of either vehicle alone (water) or vehicle containing the SGLT2 inhibitor Compound A at a dose of 0.01 mg/kg, 0.1 mg/kg and 1 mg/kg. PK/PD measurements were taken until day 4 after a single administration of compound A or its vehicle.

TABLE 2

| Pharmacokinetic data, single dose (0.01/0.1/1.0 mg/kg) | | | | |
|---|---|---|---|---|
| Parameter | | 0.01 mg/kg | 0.1 mg/kg | 1.0 mg/kg |
| $t_{max}$ [hour] | mean | 1 | 1.3 | 1 |
| $C_{max}$ [nmol/L] | mean | 9 | 77 | 1173 |
| $AUC_{0 \to \infty}$ [nmol · h/l] | mean | 30 | 358 | 5379 |
| $T_{1/2}$ [hour] | mean | 1.2 | 2.9 | 5.4 |

Pharmacodynamic Data:

A prominent increase of urinary glucose concentration was evident at doses>0.01 mg/kg already 8 h after administration (mean group values: controls 1.4 mmol/L; 0.01 mg/kg-1.4 mmol/L; 0.1 mg/kg-46.1 mmol/L; 1 mg/kg-239.3 mmol/L) and was persistent for more than 24 h.

None of the three doses of compound A altered the blood glucose level in cats as compared to normal reference values.

None of the three doses of compound A altered the renal function of cats.

Urinary glucose excretion increase is clearly dose and plasma compound exposure dependent (logarithmic-linear correlation), as shown in [0194].

Example 2 The Effect of Compound a on Urinary and Blood Glucose after Repeated Dosing in Cats Compound A was administered to overnight fasted cats. The groups (n=3 per group) received a once daily oral administration of either vehicle alone (PillPocket®) or vehicle containing the SGLT2 inhibitor (dry compound) at a dose of 1 mg/kg and 3 mg/kg for 3 consecutive days. Urinary glucose and blood glucose were measured.

A prominent increase of urinary glucose concentration was evident at both doses already 8 h after administration. The maximal urinary concentration was not further elevated after repeated dosing and was similar at doses of 1 mg/kg and 3 mg/kg (mean values-281 mmol/L and 209 mmol/L, respectively).

Neither dose of compound A altered the blood glucose level in cats as compared to normal reference values.

In respect to urinary glucose excretion it is thus estimated that the $ED_{50}$ is <1 mg/kg.

Example 3 The Effect of Compound a on Urinary and Blood Glucose after Repeated Dosing in Cats Compound A was administered to freely fed normoglycemic, obese cats. The groups (n=6 per group) received a once daily oral administration of either vehicle alone (gelatin capsules) or vehicle containing the SGLT2 inhibitor (dry compound) at a dose of 1 mg/kg for 4 weeks. Urinary glucose and blood glucose were measured.

Urinary glucose concentrations were significantly elevated at the end of the study—controls 0.6 mmol/L; 1 mg/kg-489 mmol/L.

No alterations of blood glucose levels were observed.

Example 4 Treatment of Pre-Diabetes: Prevention of Manifest Type 2 Diabetes in Cats The efficacy of SGLT2 inhibition in accordance with the invention in the treatment of pre-diabetes characterized by pathological fasting glucose and/or impaired glucose tolerance and/or insulin resistance can be tested using clinical studies. In studies over a shorter or longer period (e.g. 2-4 weeks or 1-2 years) the success of the treatment is examined by determining the fasting glucose values and/or the glucose values after a meal or after a loading test (oral glucose tolerance test or food tolerance test after a defined meal) after the end of the period of therapy for the study and comparing them with the values before the start of the study and/or with those of a placebo group. In addition, the fructosamine value can be determined before and after therapy and compared with the initial value and/or the placebo value. A significant drop in the fasting or non-fasting glucose and/or fructosamine levels demonstrates the efficacy of the treatment of pre-diabetes. Additionally a significant reduction in the number of patients who develop manifest type 2 diabetes when treated with a pharmaceutical composition according to this invention as compared to another form of treatment, demonstrates the efficacy in preventing a transition from pre-diabetes to manifest diabetes.

Example 5 Treatment of Pre-Diabetes: Improvement of Insulin Resistance in Cats

The following example shows the beneficial effect of compound A in insulin resistant obese cats. Compound A was administered to freely fed normoglycemic, insulin resistant, obese cats. The groups (n=6 per group) received a once daily oral administration of either vehicle alone (gelatin capsules) or vehicle containing the SGLT2 inhibitor (dry compound) at a dose of 1 mg/kg for 4 weeks. The following experiments were performed prior to treatment and at the end of the 4 week treatment period approximately 24 h after the last administration of compound/vehicle.

An intravenous glucose tolerance test (ivGTT, 0.8 g/kg dextrose) was performed in overnight fasted cats. Blood was collected via jugular vein catheters. Blood samples were taken at −5, 0, 5, 10, 15, 30, 45, 60, 90, 120, 180 min relative to glucose application.

Glucose and insulin excursion were quantified by calculating the baseline corrected glucose AUC. An intravenous insulin tolerance test (ivITT, 0.05 U/kg regular insulin) was performed in overnight fasted cats. Blood was collected via jugular vein catheters. Blood samples were taken at −5, 0, 15, 30, 60, 90, 120, 180 min relative to insulin application.

The excursion of glucose and non-esterified fatty acids (NEFA) was quantified by calculating baseline corrected glucose and NEFA AUC.

The significance of differences of means between groups is evaluated by repeated-measures two-factor (time & treatment) ANOVA and post hoc multiple comparisons versus control or the respective baseline readings.

The glucose excursion during the ivGTT did not change during the study period or due to the treatment. The insulin excursion was not altered throughout the study period in control cats, but was significantly reduced in treated cats as compared to baseline values ($p<0.05$).

As shown in [0195], as compared to lean cats, in the obese cats used in the present study, the insulin secretion profile exhibited a reduced first phase, and an increased and prolonged second phase. As shown in panel B of [0195], treatment with compound A led to a significant improvement of second phase insulin secretion profile.

Insulin sensitivity was significantly increased in treated cats as compared to baseline values ($p<0.05$). This was demonstrated by calculating the relationship between glucose and insulin in terms of the modified Belfiore Index ($1/\log(\Delta\Delta UCgluc*\Delta\Delta UCins)$).

Area-under-curve values of blood insulin and the blood insulin-to-glucose relationship as represented by the modified Belfiore index for insulin sensitivity in insulin resistant cats during an i.v. glucose tolerance test (ivGTT) before ("pre") and after ("post") 4 weeks of treatment with compound A or its vehicle ("control") are shown in [0196].

The glucose excursion during the ivITT significantly worsened throughout the study period in the control animals ($p<0.05$) (see [0197], panel A). This was similar for the elimination of NEFAs (see [0198], panel A). In contrast, in cats treated with compound A the glucose curve did not change throughout the study period (see [0197], panel B), and NEFA elimination was significantly improved by the compound A treatment ($p<0.01$; see [0198], panel B).

These data indicate that in obese cats insulin resistance is significantly improved after a 4 week treatment with compound A. As insulin resistance is a characteristic feature of pre-diabetes the data strongly indicate that compound A is capable of treating pre-diabetes in feline animals.

In clinical studies in diabetic cats running for different lengths of time (e.g. 2 weeks to 12 months) the success of the improvement in insulin resistance can be checked by the measuring baseline blood glucose, blood fructosamine and blood insulin levels and then monitoring the development of those levels in individual cats throughout the study period. Also the glucose and insulin values after a meal or after a loading test (glucose tolerance test or insulin tolerance test) after the end of the period of therapy for the study can be compared with the values before the start of the study and/or with those of diabetic cats who have been treated with other medications.

Example 6 Treatment of Type 2 Diabetes in Cats

Treating cats with type 2 diabetes with the pharmaceutical composition according to the invention, in addition to producing an acute improvement in the glucose metabolic situation, prevents deterioration in the metabolic situation in the long term. This can be observed if cats are treated for a shorter or longer period, e.g. 2-4 weeks or 3 months to 1 year, with the pharmaceutical composition according to the invention and are compared to the metabolic situation prior to treatment or with cats that have been treated with insulin or other antidiabetic medication. There is evidence of therapeutic success if daily mean blood glucose and fructosamine level are reduced as compared to pretreatment level. Further evidence of therapeutic success is obtained if a significantly smaller percentage of the cats treated with a pharmaceutical composition according to the invention, compared with cats who have been treated with other medications, undergo transient deterioration in the glucose metabolic position (e.g. hyper- or hypoglycemia).

Example 7 Improvement of Pancreatic Beta Cell Function

In clinical studies in diabetic cats running for different lengths of time (e.g. 4 weeks to 12 months) the success of the treatment is checked using the measurement of baseline blood glucose, blood fructosamine and blood insulin level and the corresponding relation between the parameter in the individual cat. Additionally, e.g. arginine stimulation may be employed to test the pancreatic beta cell ability to secrete insulin.

Figure 15:
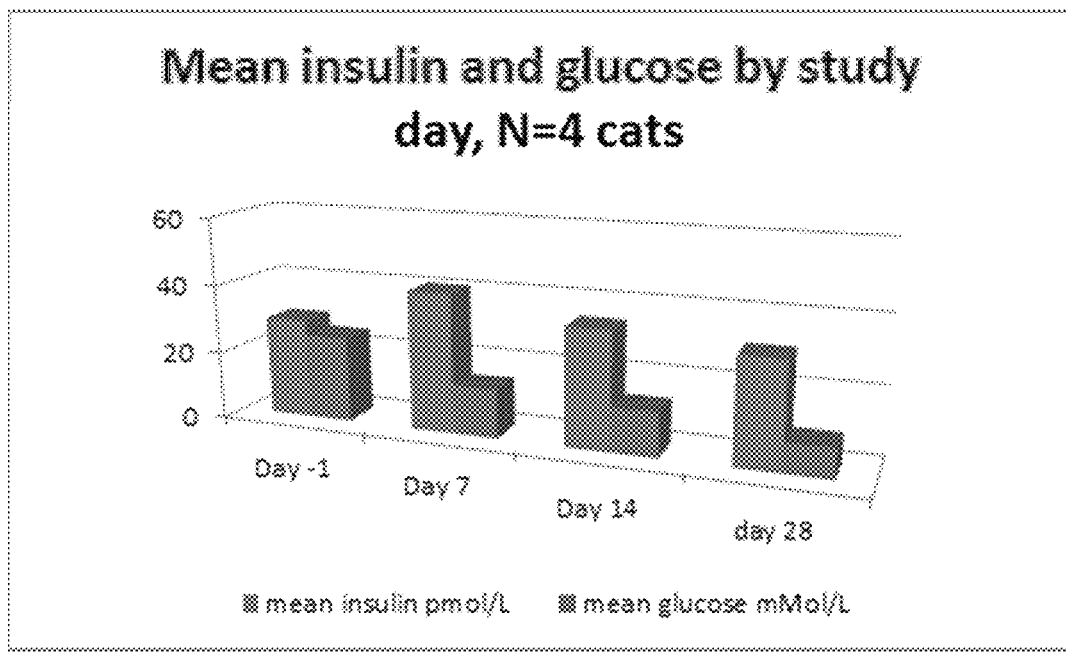
FIG. 15 Preliminary data from four cats demonstrate that fasting insulin concentrations increased compared to a simultaneous decrease of the mean glucose values (from a 9 hour blood glucose curve) at Day 7 compared to Day −1. Afterwards insulin concentrations reached a plateau which can be explained by already nearly normalized glucose concentration. This reflects the normal physiological situation in fasted animals: when glucose is within the normal range (fasted state) no increase of insulin concentrations are expected to be present any more. This preliminary data from the fasting insulin values from four cats support the claimed indications "loss of pancreatic beta cell function" and "remission of the metabolic disorder, preferably diabetic remission" since it demonstrates the increase in insulin concentrations and decrease in glucose concentrations back to a normalized values and therefore reflects the return to a normal physiological response.

A significant rise in the blood insulin level (either baseline or after arginine stimulation) during or at the end of the study, compared with the initial value or compared with a placebo group, or a group given a different therapy, proves the efficacy of a pharmaceutical composition according to the invention in the improvement of pancreatic beta cell function in diabetic cats (FIG. 15).

Example 8 Diabetic Remission

In clinical studies in diabetic cats running for a longer period (e.g. 3 months to 1 year) the success of the treatment is checked using the measurement of baseline blood glucose, blood fructosamine and blood insulin level and the corresponding relation between the parameter in the individual cat. There is evidence of therapeutic success if laboratory values are reduced as compared to pre-treatment level without the need of insulin injections (FIG. 15).

In case compound A was employed in a combination with e.g. insulin or other drugs effectively reducing hyperglycemia the feline animal may be weaned off insulin or the other drug and still have a glycemic control in normal ranges.

Most advantageously, the feline animal may be weaned of compound A.

Example 9 Reduction of Hyperglycemia

In clinical studies in diabetic cats running for different lengths of time (e.g. 1 day to 12 months) the success of the treatment in cats with hyperglycemia is checked by determining the blood glucose or blood fructosamine level. A significant fall in these values during or at the end of the study, compared with the initial value or compared with a placebo group, or a group given a different therapy, proves the efficacy of a pharmaceutical composition according to the invention in the reduction of hyperglycemia in cats.

Example 10 Body Composition and Body Fat Reduction

The following example shows the beneficial effect of compound A in obese cats. Compound A was administered to freely fed obese cats. The groups (n=6 per group) received a once daily oral administration of either vehicle alone (gelatin capsules) or vehicle containing the SGLT2 inhibitor (dry compound) at a dose of 1 mg/kg for 4 weeks. The following experiments were performed prior to treatment and at the end of the 4 week treatment period approximately 24 h after the last administration of compound/vehicle. As shown in [0199], blood leptin concentrations significantly decreased over the study period in the treated cats (mean values: pre: 2482 pmol/L, post: 2213 pmol/L, p<0.05).

Indirect calorimetry shows the influence of the treatment on energy metabolism. Respiratory exchange ratios (RER; ratio between the amount of $CO_2$ exhaled and $O_2$ inhaled; see [0200]) indicated significantly increased fatty acid metabolism (lipid utilization) in treated animals (mean RER values: 0.749 pre-treatment, 0.728 post-treatment; p<0.01).

Increased lipid utilization was also mirrored in increased blood β-hydroxybutyrate concentrations (β-HB/BHB), as shown in [0201]. The increase of blood β-hydroxybutyrate concentrations did not exceed normal reference values.

These changes in the relevant data throughout the study show a significant correlation and indicate that treatment shows a beneficial effect on body composition.

Thus, the data show a positive correlation between the change of blood leptin concentration and the change of RER before and after 4 weeks of treatment with compound A ([0202]), and a negative correlation between the blood β-hydroxybutyrate levels (β-HB/BHB) and the RER ([0203]).

Liver parameters were unchanged, and no ketones were detected in the urine. Thus, shifting of the metabolism of lipids and carbohydrates was within normal physiological ranges.

In consequence, a 4 week treatment in obese cats clearly shows that dysadipokinemia was improved and additionally shifting metabolic substrate utilization from glucose to lipid represents a clear benefit in the treatment of obese cats. The data strongly indicate that Compound A is capable of treating pre-diabetes in feline animals Example 11 Pilot Trial of Compound A in Client-Owned Diabetic Cats The following data are from 4 diabetic cats which had been prospectively treated orally with 1 mg/kg once daily Compound A for 28 days. Diagnosis of diabetes mellitus had been made on the basis of blood glucose>250 mg/dl (13.9 mmol/L) at screening, either glucosuria or serum fructosamine≥400 μmol/L, and the persistence of at least one clinical condition/sign consistent with diabetes mellitus [lethargy, polyuria, polydipsia, polyphagia, weight loss, and/or plantigrade posture of hind legs (DM polyneuropathy)].

Figure 13:
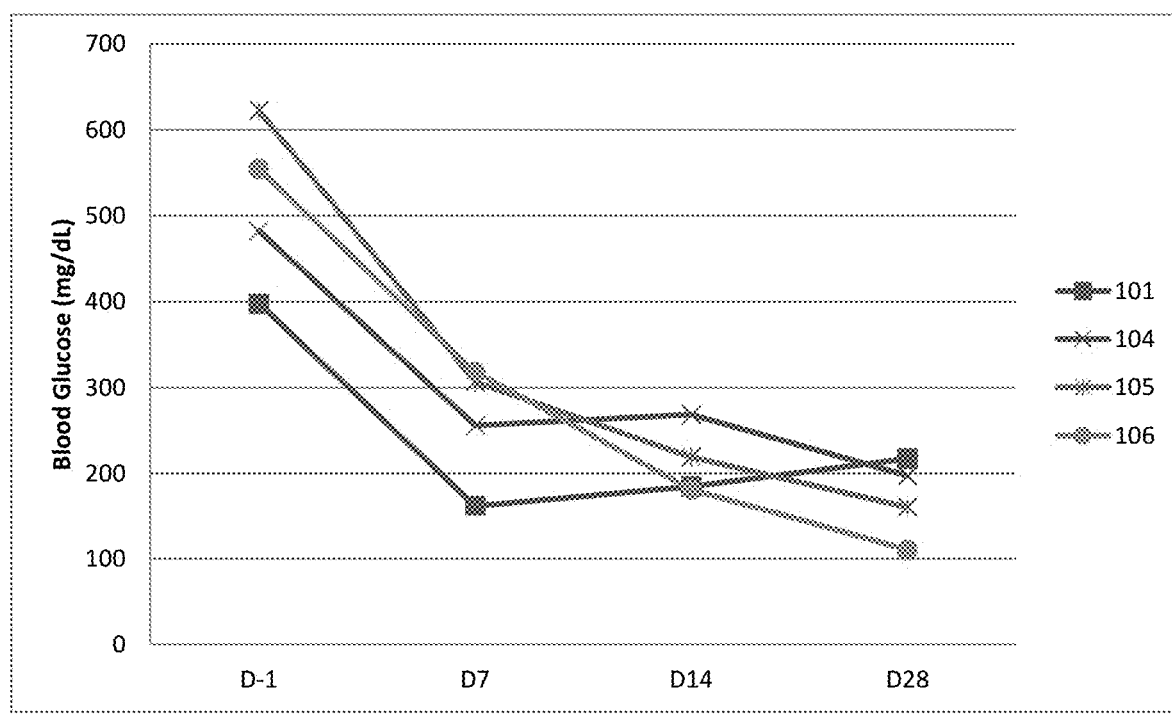
FIG. 13 shows mean blood glucose from the 9 hour glucose curve by visit day.
Figure 14:
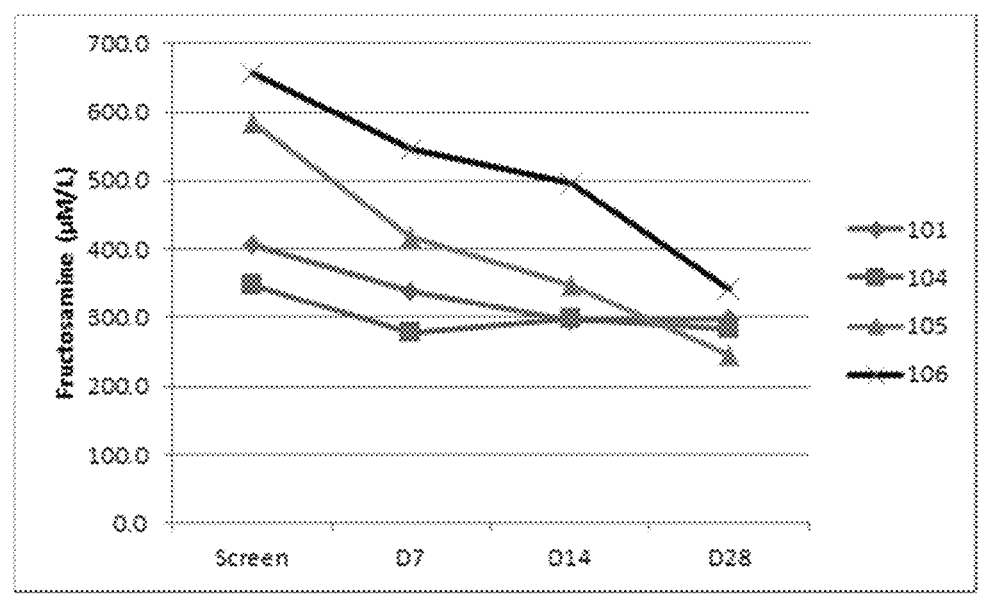
FIG. 14 shows the serum fructosamine by visit day.

Results revealed that the mean (FIG. 13) blood glucose values of the 9 hour blood glucose curve were substantially decreased in all 4 cats compared to baseline by the end of the study. The decrease was already present at day 7 and unexpectedly to such an extent comparable to long-term insulin therapy. For comparison, comparable reduction in mean blood glucose was not observed in 14 cats treated with VETSULIN® (insulin, Intervet, Inc.) until day 14 (NADA 141-236, Freedom of Information Summary, VETSULIN®). Serum fructosamine confirmed this good glycemic control and was also decreased to below 350 μmol/L (excellent control according to laboratory interpretive guidelines) in all cats by day 28 (FIG. 14). In contrast, the mean serum fructosamine for cats treated with VETSULIN® was 546 by day 30, and remained elevated at 462 on day 60 (NADA 141-236, Freedom of Information Summary, VETSULIN®).

All cats showed improvement in at least one clinical condition/sign, and 3 of 4 cats showed improvement in at least 3 clinical conditions/signs as assessed by the owner. All cats improved in overall diabetes control as assessed by the Investigator. Urinary glucose excretion was decreased in all cats by the end of the study. No hypoglycemia (defined as blood glucose less than 70 mg/dL) was reported.

In conclusion, these data demonstrate that Compound A represents can be used to treat diabetic cats with a once daily oral therapy comparable to long-term twice daily insulin therapy.

Example 12 Preparation of 1-cyano-2-(4-cyclopropyl-benzyl)-4-(β-D-glucopyranos-1-yl)-benzene (compound A)

The following example of synthesis serves to illustrate a method of preparing 1-cyano-2-(4-cyclopropyl-benzyl)-4-(β-D-glucopyranos-1-yl)-benzene (compound A). A method of preparing its crystalline complex with L-proline is also described. It is to be regarded only as a possible method described by way of example, without restriction of the scope of the invention. The terms "room temperature" and

Preparation of 4-bromo-3-hydroxymethyl-1-iodo-benzene

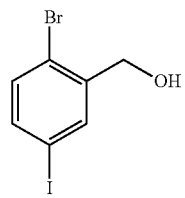

Oxalyl chloride (13.0 mL) is added to an ice-cold solution of 2-bromo-5-iodo-benzoic acid (49.5 g) in $CH_2Cl_2$ (200 mL). DMF (0.2 mL) is added and the solution is stirred at room temperature for 6 h. Then, the solution is concentrated under reduced pressure and the residue is dissolved in THF (100 mL). The resulting solution is cooled in an ice-bath and $LiBH_4$ (3.4 g) is added in portions. The cooling bath is removed and the mixture is stirred at room temperature for 1 h. The reaction mixture is diluted with THF and treated with 0.1 M hydrochloric acid. Then, the organic layer is separated and the aqueous layer is extracted with ethyl acetate. The combined organic layers are dried ($Na_2SO_4$) and the solvent is evaporated under reduced pressure to give the crude product.

Yield: 47.0 g (99% of theory)

Preparation of 4-bromo-3-chloromethyl-1-iodo-benzene

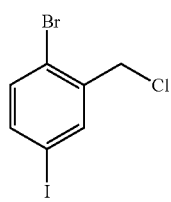

Thionyl chloride (13 mL) is added to a suspension of 4-bromo-3-hydroxymethyl-1-iodo-benzene (47.0 g) in dichloromethane (100 mL) containing DMF (0.1 mL). The mixture is stirred at ambient temperature for 3 h. Then, the solvent and the excess reagent is removed under reduced pressure. The residue is triturated with methanol and dried.

Yield: 41.0 g (82% of theory)

Preparation of 4-bromo-1-iodo-3-phenoxymethyl-benzene

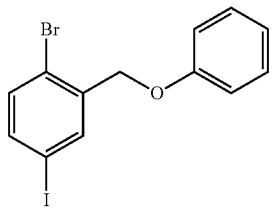 [SMILES: Brc1ccc(I)cc1COc1ccccc1]

Phenol (13 g) dissolved in 4 M KOH solution (60 mL) is added to 4-bromo-3-chloromethyl-1-iodo-benzene (41.0 g) dissolved in acetone (50 mL). NaI (0.5 g) is added and the resulting mixture is stirred at 50° C. overnight. Then, water is added and the resulting mixture is extracted with ethyl acetate. The combined extracts are dried ($Na_2SO_4$) and the solvent is evaporated under reduced pressure. The residue is purified by chromatography on silica gel (cyclohexane/ethyl acetate 19:1).

Yield: 38.0 g (79% of theory)

Preparation of 1-bromo-4-(1-methoxy-D-glucopyranos-1-yl)-2-(phenoxymethyl)-benzene

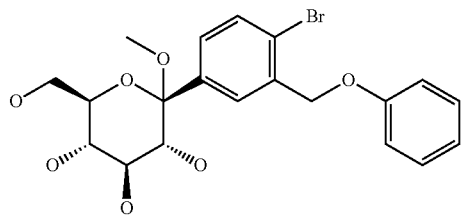 [SMILES: CO[C@@]1(c2ccc(Br)c(COc3ccccc3)c2)O[C@H](CO)[C@@H](O)[C@H](O)[C@H]1O]

A 2 M solution of iPrMgCl in THF (11 mL) is added to dry LiCl (0.47 g) suspended in THF (11 mL). The mixture is stirred at room temperature until all the LiCl is dissolved. This solution is added dropwise to a solution of 4-bromo-1-iodo-3-phenoxymethyl-benzene (8.0 g) in tetrahydrofuran (40 mL) cooled to −60° C. under argon atmosphere. The solution is warmed to −40° C. and then 2,3,4,6-tetrakis-O-(trimethylsilyl)-D-glucopyranone (10.7 g, 90% pure) in tetrahydrofuran (5 mL) is added. The resulting solution is warmed to −5° C. in the cooling bath and stirred for another 30 min at this temperature. Aqueous $NH_4Cl$ solution is added and the resultant mixture is extracted with ethyl acetate. The combined organic extracts are dried over sodium sulfate and the solvent is removed under reduced pressure. The residue is dissolved in methanol (80 mL) and treated with methane sulfonic acid (0.6 mL) to produce the more stable anomer solely. After stirring the reaction solution at 35-40° C. overnight, the solution is neutralized with solid $NaHCO_3$ and the methanol is removed under reduced pressure. The remainder is diluted with aqueous $NaHCO_3$ solution and the resulting mixture is extracted with ethyl acetate. The combined extracts are dried over sodium sulfate and the solvent is evaporated to yield the crude product that is submitted to reduction without further purification.

Yield: 7.8 g (93% of theory)

"ambient temperature" are used interchangeably and denote temperatures of about 20° C. The following abbreviations are used:

DMF dimethylformamide
NMP N-methyl-2-pyrrolidone
THF tetrahydrofuran

Preparation of 1-bromo-4-(2,3,4,6-tetra-O-acetyl-D-glucopyranos-1-yl)-2-(phenoxymethyl)-benzene

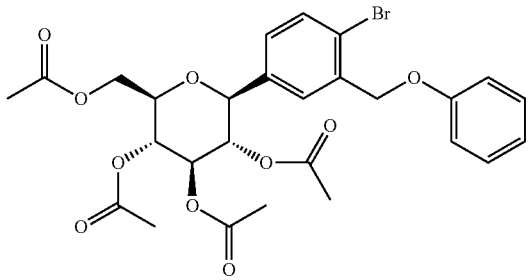 [SMILES: CC(=O)OC[C@H]1O[C@@H](c2ccc(Br)c(COc3ccccc3)c2)[C@H](OC(C)=O)[C@@H](OC(C)=O)[C@@H]1OC(C)=O]

Boron trifluoride diethyletherate (4.9 mL) is added to a solution of 1-bromo-4-(1-methoxy-D-glucopyranos-1-yl)-2-(phenoxymethyl)-benzene (8.7 g) and triethylsilane (9.1 mL) in dichloromethane (35 mL) and acetonitrile (50 mL) cooled to −20° C. at such a rate that the temperature maintains below −10° C. The resultant solution is warmed to 0° C. over a period of 1.5 h and then treated with aqueous sodium hydrogen carbonate solution. The resulting mixture is stirred for 0.5 h, the organic solvent is removed and the residue is extracted with ethyl acetate. The combined organic layers are dried over sodium sulfate and the solvent is removed. The residue is taken up in dichloromethane (50 mL) and pyridine (9.4 mL), acetic anhydride (9.3 mL) and 4-dimethylaminopyridine (0.5 g) are added in succession to the solution. The solution is stirred for 1.5 h at ambient temperature and then diluted with dichloromethane. This solution is washed twice with 1 M hydrochloric acid and dried over sodium sulfate. After the solvent is removed, the residue is recrystallized from ethanol to furnish the product as a colorless solid.

Yield: 6.78 g (60% of theory)
Mass spectrum (ESI$^+$): m/z=610/612 (Br) [M+NH$_4$]$^+$ Preparation of 2-(phenoxymethyl)-4-(2,3,4,6-tetra-O-acetyl-D-glucopyranos-1-yl)-benzonitrile

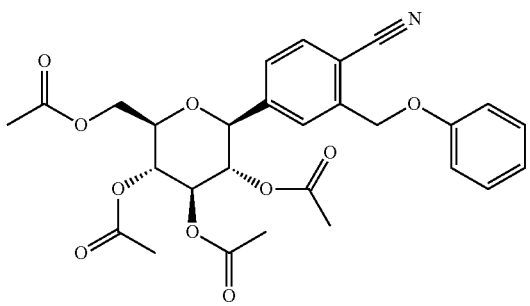 [SMILES: CC(=O)OC[C@H]1O[C@@H](c2ccc(C#N)c(COc3ccccc3)c2)[C@H](OC(C)=O)[C@@H](OC(C)=O)[C@@H]1OC(C)=O]

A flask charged with zinc cyanide (1.0 g), zinc (30 mg), Pd$_2$(dibenzylideneacetone)$_3$*CHCl$_3$ (141 mg) and tri-tert-butylphosphonium tetrafluoroborate (111 mg) is flushed with argon. Then a solution of 1-bromo-4-(2,3,4,6-tetra-O-acetyl-D-glucopyranos-1-yl)-2-(phenoxymethyl)-benzene (5.4 g) in NMP (12 mL) is added and the resulting mixture is stirred at room temperature for 18 h. After dilution with ethyl acetate, the mixture is filtered and the filtrate is washed with aqueous sodium hydrogen carbonate solution. The organic phase is dried (sodium sulfate) and the solvent is removed. The residue is recrystallized from ethanol.

Yield: 4.10 g (84% of theory)
Mass spectrum (ESI$^+$): m/z=557 [M+NH$_4$]$^+$

Alternatively, the compound described above is synthesized starting from 1-bromo-4-(2,3,4,6-tetra-O-acetyl-D-glucopyranos-1-yl)-2-(phenoxymethyl)-benzene using copper(I) cyanide (2 equivalents) in NMP at 210° C.

Preparation of 2-bromomethyl-4-(2,3,4,6-tetra-O-acetyl-D-glucopyranos-1-yl)-benzonitrile

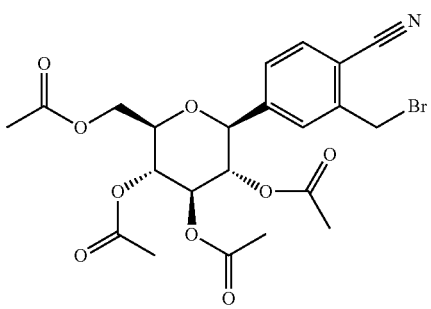 [SMILES: CC(=O)OC[C@H]1O[C@@H](c2ccc(C#N)c(CBr)c2)[C@H](OC(C)=O)[C@@H](OC(C)=O)[C@@H]1OC(C)=O]

A 33% solution of hydrobromic acid in acetic acid (15 mL) is added to a solution of 2-phenyloxymethyl-4-(2,3,4,6-tetra-O-acetyl-D-glucopyranos-1-yl)-benzonitrile (0.71 g) and acetic anhydride (0.12 mL) in acetic acid (10 ml). The resulting solution is stirred at 55° C. for 6 h and then cooled in an ice-bath. The reaction mixture is neutralized with chilled aqueous potassium carbonate solution, and the resultant mixture is extracted with ethyl acetate. The combined organic extracts are dried over sodium sulfate and the solvent is removed under reduced pressure. The residue is taken up in ethyl acetate/cyclohexane (1:5), and the precipitate is separated by filtration and dried at 50° C. to give the pure product.

Yield: 0.52 g (75% of theory)
Mass spectrum (ESI$^+$): m/z=543/545 (Br) [M+NH$_4$]$^+$ Preparation of 4-cyclopropyl-phenylboronic acid

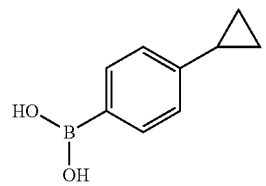 [SMILES: OB(O)c1ccc(C2CC2)cc1]

2.5 M solution of nButyllithium in hexane (14.5 mL) is added dropwise to 1-bromo-4-cyclopropyl-benzene (5.92 g) dissolved in THF (14 mL) and toluene (50 mL) and chilled to −70° C. The resultant solution is stirred at −70° C. for 30 min before triisopropyl borate (8.5 mL) is added. The solution is warmed to −20° C. and then treated with 4 M aqueous hydrochloric acid (15.5 mL). The reaction mixture is further warmed to room temperature and then the organic phase is separated. The aqueous phase is extracted with ethyl acetate and the combined organic phases are dried (sodium sulfate). The solvent is evaporated and the residue is washed with a mixture of ether and cyclohexane to give the product as a colorless solid.

Yield: 2.92 g (60% of theory)

Mass spectrum (ESI): m/z=207 (Cl) [M+HCOO]⁻

Preparation of 1-cyano-2-(4-cyclopropyl-benzyl)-4-(β-D-glucopyranos-1-yl)-benzene

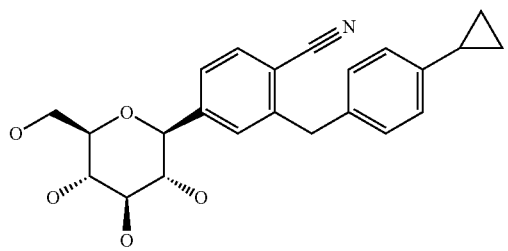 [SMILES: N#Cc1ccc([C@@H]2O[C@H](CO)[C@@H](O)[C@H](O)[C@H]2O)cc1Cc1ccc(C2CC2)cc1]

An Ar filled flask is charged with 2-bromomethyl-4-(2,3,4,6-tetra-O-acetyl-D-glucopyranos-1-yl)-benzonitrile (1.60 g), 4-cyclopropyl-phenylboronic acid (1.0 g), potassium carbonate (1.85 g) and a degassed 3:1 mixture of acetone and water (22 mL). The mixture is stirred at room temperature for 5 min, before it is cooled in an ice-bath. Then palladium dichloride (30 mg) is added and the reaction mixture is stirred for 16 h at ambient temperature. The mixture is then diluted with brine and extracted with ethyl acetate. The combined extracts are dried over sodium sulfate and the solvent is removed under reduced pressure. The residue is dissolved in methanol (20 mL) and treated with 4 M aqueous potassium hydroxide solution (4 mL). The resulting solution is stirred at ambient temperature for 1 h and then neutralized with 1 M hydrochloric acid. The methanol is evaporated, and the residue is diluted with brine and extracted with ethyl acetate. The organic extracts collected are dried over sodium sulfate, and the solvent is removed. The residue is chromatographed on silica gel (dichloromethane/methanol 1:0→8:1).

Yield: 0.91 g (76% of theory)

Mass spectrum (ESI⁺): m/z=413 [M+NH₄]⁺

Preparation of a Crystalline Complex (1:1) of Compound A with L-Proline

L-proline (0.34 g) dissolved in 2.1 mL of a mixture of ethanol and water (volume ratio 10:1) is added to a solution of 1-cyano-2-(4-cyclopropyl-benzyl)-4-(β-D-glucopyranos-1-yl)-benzene (1.17 g, obtained as described above) dissolved in 2 mL ethanol. The resulting solution is allowed to stand at ambient temperature. After about 16 h the crystalline complex is isolated as white crystals by filtration. If necessary the crystallization may be initiated by scratching with a glass rod or metal spatula for example or by inoculating with seed crystals. Residual solvent is removed by storing the crystals at slightly elevated temperature (30 to 50° C.) under vacuum for about 4 h to yield 1.27 g of the crystalline 1:1 complex of L-proline and 1-cyano-2-(4-cyclopropyl-benzyl)-4-(β-D-glucopyranos-1-yl)-benzene.

Figure 11:
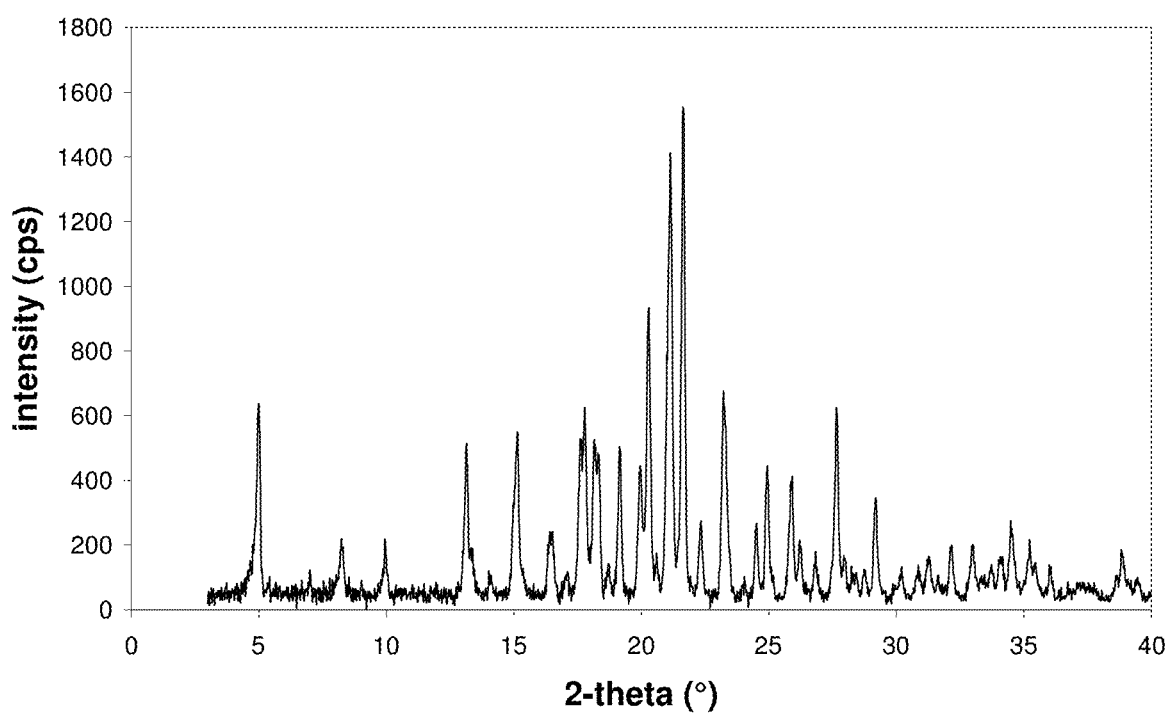
FIG. 11 shows an X-ray powder diffraction pattern of a representative batch of a crystalline complex of compound A with L-proline (1:1).
Figure 12:
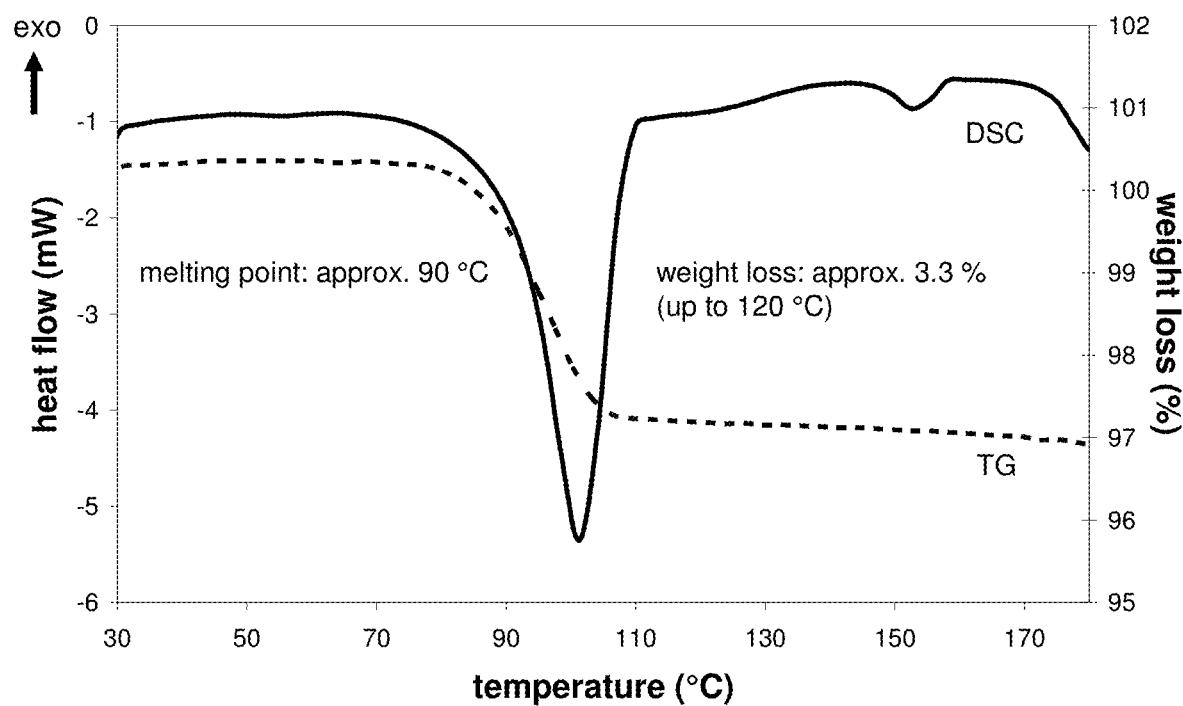
FIG. 12 shows a DSC/TG diagram of a representative batch of a crystalline complex of compound A with L-proline (1:1).

Several batches of the crystalline complex according to the above preparation are obtained. The X-ray powder diffraction patterns coincide. The melting points are determined via DSC and evaluated as onset-temperature. Examples of melting points are approximately 89° C., 90° C., 92° C., 101° C. and 110° C. The X-ray powder diffraction pattern as contained in Table 1 and as depicted in FIG. 11 and the DSC and TG diagram in FIG. 12 correspond to a batch with a melting point of approximately 90° C.

The X-ray powder diffraction pattern of the crystalline complex of the compound A and L-proline (peaks up to 30° in 2 Θ) is provided above in Table 1.

Example 13 Formulations

Some examples of formulations are described in which the term "active substance" denotes an SGLT2 inhibitor or pharmaceutically acceptable form thereof, e.g. a prodrug or a crystalline form, for use according to the invention. In the case of a combination with one or additional active substances, the term "active substance" may also include the additional active substance.

Tablets Containing 100 mg of Active Substance

Composition:

| 1 tablet contains: | |
| --- | --- |
| active substance | 100.0 mg |
| lactose | 80.0 mg |
| corn starch | 34.0 mg |
| polyvinylpyrrolidone | 4.0 mg |
| magnesium stearate | 2.0 mg |
| | 220.0 mg |

Method of Preparation:

The active substance, lactose and starch are mixed together and uniformly moistened with an aqueous solution of the polyvinylpyrrolidone. After the moist composition has been screened (2.0 mm mesh size) and dried in a rack-type drier at 50° C. it is screened again (1.5 mm mesh size) and the lubricant is added. The finished mixture is compressed to form tablets.

Weight of tablet: 220 mg

Diameter: 10 mm, biplanar, facetted on both sides and notched on one side.

Tablets Containing 150 mg of Active Substance

Composition:

| 1 tablet contains: | |
| --- | --- |
| active substance | 150.0 mg |
| powdered lactose | 89.0 mg |
| corn starch | 40.0 mg |
| colloidal silica | 10.0 mg |
| polyvinylpyrrolidone | 10.0 mg |
| magnesium stearate | 1.0 mg |
| | 300.0 mg |

Preparation:

The active substance mixed with lactose, corn starch and silica is moistened with a 20% aqueous polyvinylpyrrolidone solution and passed through a screen with a mesh size of 1.5 mm. The granules, dried at 45° C., are passed through the same screen again and mixed with the specified amount of magnesium stearate. Tablets are pressed from the mixture.

Weight of tablet: 300 mg die: 10 mm, flat

Hard Gelatin Capsules Containing 150 mg of Active Substance
Composition:

| 1 capsule contains: | |
|---|---|
| active substance | 150.0 mg |
| corn starch (dried) | approx. 180.0 mg |
| lactose (powdered) | approx. 87.0 mg |
| magnesium stearate | 3.0 mg |
| | approx. 420.0 mg |

Preparation:
The active substance is mixed with the excipients, passed through a screen with a mesh size of 0.75 mm and homogeneously mixed using a suitable apparatus. The finished mixture is packed into size 1 hard gelatin capsules.
Capsule filling: approx. 320 mg
Capsule shell: size 1 hard gelatin capsule.
Suppositories Containing 150 mg of Active Substance
Composition:

| 1 suppository contains: | |
|---|---|
| active substance | 150.0 mg |
| polyethylene glycol 1500 | 550.0 mg |
| polyethylene glycol 6000 | 460.0 mg |
| polyoxyethylene sorbitan monostearate | 840.0 mg |
| | 2,000.0 mg |

Preparation:
After the suppository mass has been melted the active substance is homogeneously distributed therein and the melt is poured into chilled molds.
Ampoules Containing 10 mg Active Substance
Composition:

| active substance | 10.0 mg |
|---|---|
| 0.01N hydrochloric acid/NaCl | q.s. |
| double-distilled water | ad 2.0 ml |

Preparation:
The active substance is dissolved in the necessary amount of 0.01 N HCl, made isotonic with common salt, filtered sterile and transferred into 2 ml ampoules.
Ampoules Containing 50 mg of Active Substance
Composition:

| active substance | 50.0 mg |
|---|---|
| 0.01N hydrochloric acid/NaCl | q.s. |
| double-distilled water | ad 10.0 ml |

Preparation:
The active substance is dissolved in the necessary amount of 0.01 N HCl, made isotonic with common salt, filtered sterile and transferred into 10 ml ampoules.

REFERENCES

1) Curry et al., Comp Biochem Physiol. 1982. 72A(2): 333-338
2) EP 1 213 296
3) EP 1 354 888
4) EP 1 344 780
5) EP 1 489 089
6) Hoenig, Mol Cell Endocrinol 2002, 197(1-2): 221-229
7) Hoenig et al., Am J Physiol, 2011, 301(6):R1798-1807
8) NADA 141-236 Freedom of Information VETSULIN®
9) Palm C A et al., Vet Clin Small Anim 2013, 43: 407-415
10) Reusch C E et al., Schweizer Archiv fuer Tierheilkunde 2011, 153811): 495-500
11) Tanaka et al., Vet Res Commun 2005, 29(6):477-485
12) Verbrugghe et al., Crit Rev Food Sci Nutr. 2012; 52(2):172-182
13) WO 01/27128
14) WO 03/099836
15) WO 2004/007517
16) WO 2004/080990
17) WO 2005/012326
18) WO 2005/092877
19) WO 2006/034489
20) WO 2006/064033
21) WO 2006/117359
22) WO 2006/117360
23) WO 2006/120208
24) WO 2007/025943
25) WO 2007/028814
26) WO 2007/031548
27) WO 2007/093610
28) WO 2007/114475
29) WO 2007/128749
30) WO 2007/140191
31) WO 2008/002824
32) WO 2008/013280
33) WO 2008/042688
34) WO 2008/049923
35) WO 2008/055870
36) WO 2008/055940
37) WO 2008/069327
38) WO 2008/116179
39) WO 2009/014970
40) WO 2009/022008
41) WO 2009/022020
42) WO 2009/035969
43) WO 2010/023594
44) WO 2011/039107
45) WO 2011/039108
46) WO 2011/117295
47) WO 2014/016381

The above references are incorporated by reference.

The invention claimed is:
1. A method of treatment or prevention of a metabolic disorder in a feline animal comprising administering to the feline animal a composition that comprises an SGLT2 inhibitor or pharmaceutically acceptable form thereof, wherein the SGLT2 inhibitor or pharmaceutically acceptable form thereof consists of 1-cyano-2-(4-cyclopropyl-benzyl)-4-(β-D-glucopyranos-1-yl)-benzene, represented by the following formula:

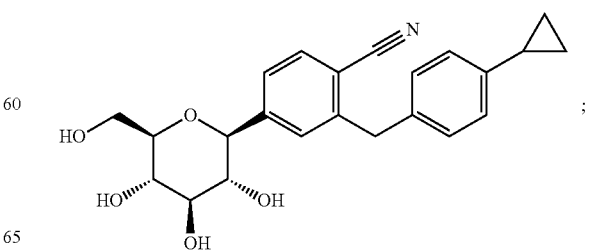

wherein:
the metabolic disorder is selected from the group consisting of ketoacidosis, pre-diabetes, diabetes mellitus type 1, diabetes mellitus type 2, insulin resistance, obesity, hyperglycemia, impaired glucose tolerance, hyperinsulinemia, dyslipidemia, dysadipokinemia, subclinical inflammation, systemic inflammation, low grade systemic inflammation, hepatic lipidosis, atherosclerosis, inflammation of the pancreas, neuropathy, Syndrome X (metabolic syndrome), loss of pancreatic beta cell function, diabetic remission, and combinations thereof; and
said SGLT2 inhibitor or pharmaceutically acceptable form thereof is administered at a dose from 0.1 to 1 mg/kg body mass per day.

2. The method according to claim 1, wherein the metabolic disorder is selected from the group consisting of pre-diabetes, diabetes mellitus type 1, diabetes mellitus type 2, and clinical conditions associated with pre-diabetes, diabetes mellitus type 1 or diabetes mellitus type 2.

3. The method according to claim 2, wherein said metabolic disorder is pre-diabetes, diabetes mellitus type 2 or a clinical condition associated with pre-diabetes or diabetes mellitus type 2.

4. The method according to claim 2, wherein said clinical condition is a condition selected from the group consisting of ketoacidosis, insulin resistance, obesity, hyperglycemia, impaired glucose tolerance, hyperinsulinemia, dyslipidemia, dysadipokinemia, subclinical inflammation, systemic inflammation, low grade systemic inflammation, hepatic lipidosis, atherosclerosis, inflammation of the pancreas, neuropathy, Syndrome X (metabolic syndrome), loss of pancreatic beta cell function, diabetic remission, and combinations thereof.

5. The method according to claim 1, wherein said ketoacidosis, insulin resistance, obesity, hyperglycemia, impaired glucose tolerance, hyperinsulinemia, dyslipidemia, dysadipokinemia, subclinical inflammation, systemic inflammation, low grade systemic inflammation, hepatic lipidosis, atherosclerosis, inflammation of the pancreas, neuropathy and/or Syndrome X (metabolic syndrome), of pancreatic beta cell function and/or diabetic remission is associated with diabetes.

6. The method according to claim 5, wherein said diabetes is pre-diabetes or diabetes mellitus type 2.

7. The method according to claim 1, wherein the feline animal is obese.

8. The method according to claim 1, wherein the feline animal is suffering from diabetes.

9. The method according to claim 8, wherein said diabetes is pre-diabetes or diabetes mellitus type 2.

10. The method according to claim 1, wherein the feline animal is a cat.

11. The method according to claim 1, wherein said inhibitor or pharmaceutically acceptable form thereof is administered only once per day.

12. The method according to claim 1, further comprising administering to the feline animal a combination of insulin and the SGLT2 inhibitor or pharmaceutically acceptable form thereof.

13. The method according to claim 12, wherein the composition comprises a 1:1 crystalline complex of the SGLT2 inhibitor or pharmaceutically acceptable form thereof and an amino acid, and the crystalline complex is a crystalline hydrate.

14. The method according to claim 13, wherein said amino acid comprises proline.

15. The method according to claim 14, wherein said amino acid comprises L-proline.

16. A method of treatment or prevention of a metabolic disorder in a feline animal comprising administering to the feline animal a composition that comprises an SGLT2 inhibitor or pharmaceutically acceptable form thereof at a dose from 0.01 to 5.0 mg/kg body mass per day, wherein the SGLT2 inhibitor or pharmaceutically acceptable form thereof consists of 1-cyano-2-(4-cyclopropyl-benzyl)-4-(β-D-glucopyranos-1-yl)-benzene, represented by the following formula:

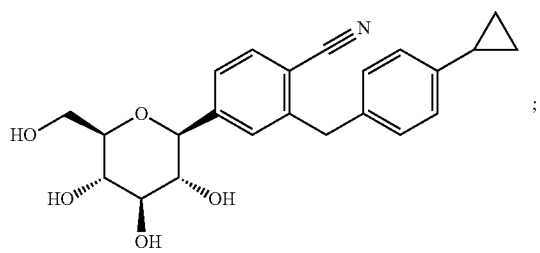 [SMILES: N#Cc1ccc([C@@H]2O[C@H](CO)[C@@H](O)[C@H](O)[C@H]2O)cc1Cc1ccc(C2CC2)cc1]

wherein:
the metabolic disorder is selected from the group consisting of ketoacidosis, pre-diabetes, diabetes mellitus type 1, diabetes mellitus type 2, insulin resistance, obesity, hyperglycemia, impaired glucose tolerance, hyperinsulinemia, dyslipidemia, dysadipokinemia, subclinical inflammation, systemic inflammation, low grade systemic inflammation, hepatic lipidosis, atherosclerosis, inflammation of the pancreas, neuropathy, Syndrome X (metabolic syndrome), loss of pancreatic beta cell function, diabetic remission, and combinations thereof; and
the composition comprises a 1:1:1 crystalline complex of the SGLT2 inhibitor or pharmaceutically acceptable form thereof, L-proline and water in a crystalline form.

17. The method according to claim 16, wherein the 1:1:1 crystalline complex is characterized by an X-ray powder diffraction pattern that comprises peaks at 20.28, 21.14 and 21.64 degrees 2Θ (±0.1 degrees 2Θ), wherein said X-ray powder diffraction pattern is made using $CuK_{\alpha 1}$ radiation.

18. A method of treatment or prevention of a metabolic disorder in a feline animal comprising administering to the feline animal a composition that comprises an SGLT2 inhibitor or pharmaceutically acceptable form thereof at a dose from 0.01 to 5.0 mg/kg body mass per day, wherein the SGLT2 inhibitor or pharmaceutically acceptable form thereof consists of 1-cyano-2-(4-cyclopropyl-benzyl)-4-(β-D-glucopyranos-1-yl)-benzene, represented by the following formula:

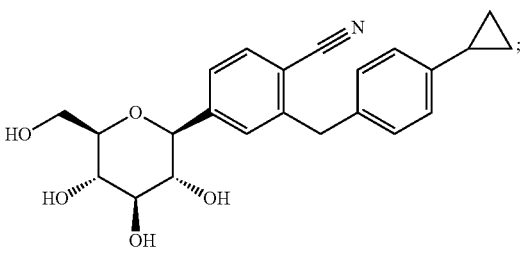 [SMILES: N#Cc1ccc([C@@H]2O[C@H](CO)[C@@H](O)[C@H](O)[C@H]2O)cc1Cc1ccc(C2CC2)cc1]

wherein:

the metabolic disorder is selected from the group consisting of ketoacidosis, pre-diabetes, diabetes mellitus type 1, diabetes mellitus type 2, insulin resistance, obesity, hyperglycemia, impaired glucose tolerance, hyperinsulinemia, dyslipidemia, dysadipokinemia, subclinical inflammation, systemic inflammation, low grade systemic inflammation, hepatic lipidosis, atherosclerosis, inflammation of the pancreas, neuropathy, Syndrome X (metabolic syndrome), loss of pancreatic beta cell function, diabetic remission, and combinations thereof; and the composition comprises a 1:1 crystalline complex of the SGLT2 inhibitor or pharmaceutically acceptable form thereof and an amino acid, and the crystalline complex is a crystalline hydrate.

* * * * *

UNITED STATES PATENT AND TRADEMARK OFFICE
CERTIFICATE OF CORRECTION

PATENT NO. : 10,617,666 B2
APPLICATION NO. : 14/573352
DATED : April 14, 2020
INVENTOR(S) : Reiche et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 171 days.

Signed and Sealed this
Thirteenth Day of December, 2022

*Katherine Kelly Vidal*

Katherine Kelly Vidal
*Director of the United States Patent and Trademark Office*